United States Patent
Zhang et al.

(10) Patent No.: US 12,129,221 B2
(45) Date of Patent: Oct. 29, 2024

(54) DIFLUORO PHENYL AMIDE RIP1 INHIBITOR

(71) Applicant: SIRONAX LTD, Grand Cayman (KY)

(72) Inventors: Zhiyuan Zhang, Beijing (CN); Yaning Su, Beijing (CN); Yi Yang, Beijing (CN); Guozheng Wang, Beijing (CN); Wendong Liu, Beijing (CN); Yongfen Ma, Beijing (CN); Yan Ren, Beijing (CN)

(73) Assignee: SIRONAX LTD, Grand Cayman (KY)

( * ) Notice: Subject to any disclaimer, the term of this patent is extended or adjusted under 35 U.S.C. 154(b) by 723 days.

(21) Appl. No.: 17/325,193

(22) Filed: May 19, 2021

(65) Prior Publication Data

US 2021/0284598 A1    Sep. 16, 2021

Related U.S. Application Data

(63) Continuation of application No. PCT/CN2019/119676, filed on Nov. 20, 2019.

(30) Foreign Application Priority Data

Nov. 20, 2018    (WO) ................ PCT/CN2018/116555

(51) Int. Cl.
*C07C 233/13*    (2006.01)
*A61P 25/28*    (2006.01)
*A61P 31/12*    (2006.01)
*A61P 35/00*    (2006.01)

(52) U.S. Cl.
CPC ............ *C07C 233/13* (2013.01); *A61P 25/28* (2018.01); *A61P 31/12* (2018.01); *A61P 35/00* (2018.01)

(58) Field of Classification Search
CPC ..... C07C 233/13; C07C 259/08; A61P 25/28; A61P 31/12; A61P 35/00; A61P 25/00; A61P 31/00; A61K 31/16
See application file for complete search history.

(56) References Cited

U.S. PATENT DOCUMENTS 9,974,762 B2 *   5/2018   Zhang .................... C07C 25/02

FOREIGN PATENT DOCUMENTS

WO    WO-2016101885 A1 *   6/2016   ............. A61K 31/10

* cited by examiner

Primary Examiner — Kortney L. Klinkel
Assistant Examiner — Dawanna Shar-Day White
(74) Attorney, Agent, or Firm — Richard Aron Osman

(57) ABSTRACT

The disclosed compounds inhibit cellular necrosis, and include corresponding sulfonamides, prodrugs and pharmaceutically acceptable salts, hydrates and stereoisomers thereof. The compounds are employed in pharmaceutical compositions, and methods of making and use, including treating a person in need thereof with an effective amount of the compound or composition, and detecting a resultant improvement in the person's health or condition.

4 Claims, No Drawings

DIFLUORO PHENYL AMIDE RIP1 INHIBITOR

INTRODUCTION

Tumor necrosis factor alpha (TNF-α)-induced NF-κB activation plays a central role in the immune system and inflammatory responses. Receptor-interacting protein 1 (RIP1) is a multi-functional signal transducer involved in mediating nuclear factor κB (NF-κB) activation, apoptosis, and necroptosis. The kinase activity of RIP1 is critically involved in mediating necroptosis, a caspase-independent pathway of necrotic cell death. Holler et al. Nat Immunol 2000; 1: 489-495; Degterev et al. Nat Chem Biol 2008; 4: 313-321.

Necroptosis plays a role in various pathological forms of cell death, including ischemic brain injury, neurodegenerative diseases and viral infections. Dunai, et al., December 2011, Pathol. Oncol. Res.: POR 17 (4): 791-800. Necrostatin-1 (Nec-1), a small molecule inhibitor of RIP1 kinase activity, can block necroptosis. Degterev et al. Nat Chem Biol 2005; 1: 112-119.

RIP1 can contribute to D-1 immunotherapy resistance (e.g. Manguso et al., 2017 Nature 547, 413-418) and can act as a checkpoint kinase governing tumor immunity (e.g. Wang et al, Cancer Cell 34, 757-774, Nov. 12, 2018).

Related patent publications include: U.S. Pat. No. 9,974,762, U.S. Ser. No. 10/092,529, U.S. Pat. Nos. 6,756,394, 8,278,344, US2012122889, US2009099242, US2010317701, US2011144169, US20030083386, US20120309795, WO2009023272, WO2010075290, WO2010075561, WO2012125544.

SUMMARY OF THE INVENTION

The invention provides compounds that are inhibitors of necrosis, ferroptosis, human receptor interacting protein 1 kinase (RIP1) or related indications, and prodrugs thereof, which are hydrolyzed, typically in the gut or blood, to yield the corresponding inhibitors. The inhibitors provide unexpectedly exceptional metabolic stability, evidenced by liver microsome data and PK data.

In an aspect the invention provides a prodrug compound of an inhibitor of necrosis, ferroptosis, human RIP1, or related indications, the compound of structure:

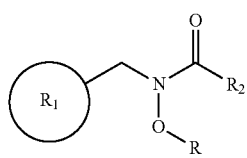

wherein R is CO(R3), PO(OR4)$_2$ or COR5:

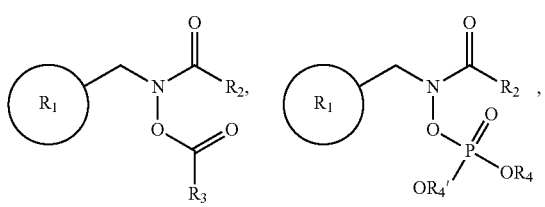

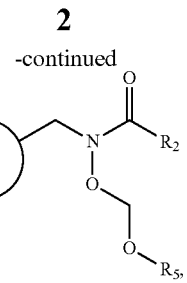

wherein:
R$_1$ is C5 or C6 aryl;
R$_2$ is substituted or unsubstituted, 0-3 heteroatom hydrocarbyl or substituted heteroatom;
R$_3$ is substituted or unsubstituted, 0-3 heteroatom hydrocarbyl or substituted heteroatom;
R$_4$ and R$_{4'}$ are independently H or CH$_3$;
R$_5$ is substituted or unsubstituted, 0-3 heteroatom hydrocarbyl or substituted heteroatom; r
a pharmaceutically acceptable salt, hydrate or stereoisomer of the compound.

In embodiments:
the compound is of structure:

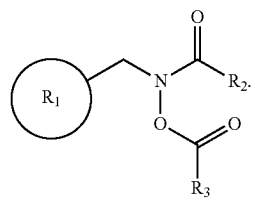

R$_1$ is: (a) substituted or unsubstituted phenyl;
(b) substituted or unsubstituted 2-, 3- or 4-pyridine;
(c) substituted or unsubstituted pyrimidine; or
(d) substituted or unsubstituted thiophene.
R$_1$ is halide-substituted or unsubstituted phenyl;
R$_1$ is 3,5 difluorophenyl;
R$_2$ is 1,1-dimethylpropyl, 1,1-dimethylprop-2-enyl, or 1,1-dimethylprop-2-ynyl, each optionally fluorinated with 1-4 F atoms;
R$_3$ is OEt, pyridine, OEtOMe, or OEtOEtOMe;
R$_5$ is COC(CH$_3$)$_3$;
the compound comprises one or more deuterium isotopes; and/or
R$_2$ is 1,1-dimethylpropyl and the compound comprises 2 or 4 deuterium isotopes.

In another aspect the invention provides an amide compound that is an inhibitor of necrosis, ferroptosis, RIP1, or related indications, or prodrug thereof, the compound of structure:

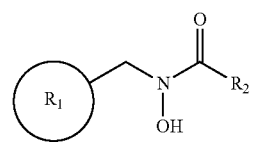

wherein:
R$_1$ is halide-substituted or unsubstituted phenyl;
R$_2$ is 1,1-dimethylpropyl, 1,1-dimethylprop-2-enyl, or 1,1-dimethylprop-2-ynyl, each optionally fluorinated with 1-4 F atoms; a pharmaceutically acceptable salt, hydrate, sulfonamide or stereoisomer of the compound.

In embodiments:

R₁ is halide-substituted or unsubstituted phenyl;

the compound comprises one or more deuterium isotopes.

R₂ is 1,1-dimethylpropyl comprising 2 or 4 deuterium isotopes.

In another aspect the invention provides a compound that is an inhibitor of necrosis, ferroptosis, human RIP1, or related indications, or sulfonamide or prodrug thereof, the compound of a structure of Table 1 or 2, respectively, particularly compounds 2, 13, 15, 19, 26, 27, 28, 29 30 and 31, more particularly compounds 13 and 26.

In another aspect the invention provides a mixture of a disclosed prodrug and a corresponding inhibitor of necrosis, ferroptosis, human RIP1, or related indications, or a mixture of a disclosed compound that is an inhibitor of necrosis, ferroptosis, human RIP1, or related indications, and a prodrug thereof.

In another aspect the invention provides pharmaceutical compositions comprising the disclosed compounds or mixtures, preferably in unit form and dosage, and one or more pharmaceutically acceptable excipients.

In another aspect the invention provides use of a disclosed compound, mixture or composition in the manufacture of a medicament for inhibiting necrosis, ferroptosis, human RIP1, or related indications in a person in need thereof.

In another aspect the invention provides use of a disclosed compound, mixture or composition for inhibiting necrosis, ferroptosis, human RIP1, or related indications in a person in need thereof, or in the manufacture of a medicament therefor in a person in need thereof.

In another aspect the invention provides a method of inhibiting necrosis, ferroptosis, human RIP1, or related indications, comprising administering to a person in need thereof a disclosed compound, mixture or composition.

In embodiments the related indications are such as brain injury, neurodegenerative diseases, viral infections, immune tolerance, and cancer e.g. promote tumor immunity in pancreatic cancer and melanoma.

The invention encompasses all combination of the particular embodiments recited herein, as if each combination had been laboriously recited.

DESCRIPTION OF PARTICULAR EMBODIMENTS OF THE INVENTION

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The term "alkyl" refers to a hydrocarbon group selected from linear and branched saturated hydrocarbon groups of 1-18, or 1-12, or 1-6 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

Lower alkyl means 1-8, preferably 1-6, more preferably 1-4 carbon atoms; lower alkenyl or alkynyl means 2-8, 2-6 or 2-4 carbon atoms.

The term "alkenyl" refers to a hydrocarbon group selected from linear and branched hydrocarbon groups comprising at least one C=C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halogen" or "halo" refers to F, Cl, Br or I.

The term "heteroalkyl" refers to alkyl comprising at least one heteroatom.

The term "heteroaryl" refers to a group selected from:
- 5- to 7-membered aromatic, monocyclic rings comprising 1, 2, 3 or 4 heteroatoms selected from N, O, and S, with the remaining ring atoms being carbon;
- 8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and
- 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

In embodiments substituents are selected from optionally substituted heteroatom and optionally substituted, optionally hetero-, optionally cyclic C1-C18 hydrocarbyl, particularly wherein the optionally substituted, optionally hetero-, optionally cyclic C1-C18 hydrocarbyl is optionally-substituted, optionally hetero-, optionally cyclic alkyl, alkenyl or alkynyl, or optionally-substituted, optionally hetero-aryl; and/or the optionally substituted heteroatom is halogen, optionally substituted hydroxyl (such as alkoxy, aryloxy), optionally substituted acyl (such as formyl, alkanoyl, carbamoyl, carboxyl, amido), optionally substituted amino (such as amino, alkylamino, dialkylamino, amido, sulfamidyl), optionally substituted thiol (such as mercapto, alkylthiol, aryl thiol), optionally substituted sulfinyl or sulfonyl (such as alkylsulfinyl, arylsulfinyl, alkyl sulfonyl, arylsulfonyl), nitro, or cyano.

In embodiments, substituents are selected from: halogen, —R', —OR', =O, =NR', =N—OR', —NR'R", —SR', —SiR'R"R''', —OC(O)R', —C(O)R', —CO2R', —CONR'R", —OC(O)NR'R", —NR"C(O)R', —NR'—C(O)NR"R''', —NR'—SO2NR''', —NR"CO2R', —NH—C(NH2)=NH, —NR'C(NH2)=NH, —NH—C(NH2)=NR', —S(O)R', —SO2R', —SO2NR'R", —NR"SO2R, —CN and —NO2, —N3, —CH(Ph)2, perfluoro(C1-C4)alkoxy and perfluoro(C1-C4)alkyl, in a number ranging from zero to three, with those groups having zero, one or two substituents being particularly preferred. R', R" and R'" each independently refer to hydrogen, unsubstituted (C1-C8)alkyl and heteroalkyl, (C1-C8)alkyl and heteroalkyl substituted with one to three halogens, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. Hence, —NR'R" includes 1-pyrrolidinyl and 4-morpholinyl, "alkyl" includes groups such as trihaloalkyl (e.g., —CF3 and —CH2CF3), and when the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl".

Preferred substituents are selected from: halogen, —R', —OR', =O, —NR'R", —SR', —SiR'R"R'", —OC(O)R', —C(O)R', —CO2R', —CONR'R", —OC(O)NR'R", —NR"C(O)R', —NR"CO2R', —NR'—SO2NR"R'", —S(O) R', —SO2R', —SO2NR'R", —NR"SO2R, —CN and —NO2, perfluoro(C1-C4)alkoxy and perfluoro(C1-C4)alkyl, where R' and R" are as defined above.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, 0-3 heteroatom C1-C6 alkyl, substituted or unsubstituted, 0-3 heteroatom C2-C6 alkenyl, substituted or unsubstituted, 0-3 heteroatom C2-C6 alkynyl, or substituted or unsubstituted, 0-3 heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, iscyanate, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3).

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents. Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—(CH$_2$)n-COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" refers to administering at least one compound and/or at least one stereoisomer thereof, and/or at least one pharmaceutically acceptable salt thereof to a subject in recognized need thereof.

An "effective amount" refers to an amount of at least one compound and/or at least one stereoisomer thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent $R^{16}$" herein includes from 1 to 4, such as from 1 to 3, further as 1 or 2, substituents selected from the list of $R^{16}$ as described herein.

The subject compounds and stereoisomers thereof, and pharmaceutically acceptable salts thereof may be employed alone or in combination with at least one other therapeutic agent for treatment. In some embodiments, the compounds, stereoisomers thereof, and pharmaceutically acceptable salts thereof can be used in combination with at least one additional therapeutic agent. The compound and/or one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the compound and/or one pharmaceutically acceptable salt disclosed herein.

Also provided is a composition comprising a subject compound and stereoisomers thereof, and pharmaceutically acceptable salts thereof, and at least one pharmaceutically acceptable carrier.

The composition comprising a subject compound and stereoisomers thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The subject compounds and stereoisomers thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The subject compounds and stereoisomers thereof, and pharmaceutically acceptable salts thereof disclosed herein can also be administered parenterally, in sterile liquid dosage forms, such as dispersions, suspensions or solutions. Other dosages forms that can also be used to administer the subject compounds and stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene gycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in *Remington's Pharmaceutical Sciences*, A. Osol, a standard reference text in the art.

For administration by inhalation, the subject compounds and stereoisomers thereof, and pharmaceutically acceptable salts thereof may be conveniently delivered in the form of an aerosol spray presentation from pressurized packs or nebulisers. The subject compounds and stereoisomers thereof, and pharmaceutically acceptable salts thereof may also be delivered as powders, which may be formulated and the powder composition may be inhaled with the aid of an insufflation powder inhaler device. One exemplary delivery system for inhalation can be metered dose inhalation (MDI) aerosol, which may be formulated as a suspension or solution of a subject compound and stereoisomers thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the subject compound and stereoisomers thereof, and pharmaceutically acceptable salts thereof in an appropriate ophthalmic vehicle, such that the subject compound and stereoisomers thereof, and at least one pharmaceutically acceptable salts thereof is maintained in contact with the ocular surface for a sufficient time period to allow the compound to penetrate the corneal and internal regions of the eye.

Useful pharmaceutical dosage-forms for administration of the subject compounds and stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the subject compound and stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the compound, stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound, stereoisomers thereof, and pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound, stereoisomers thereof, and pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound, stereoisomers thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The compounds, stereoisomers thereof, and pharmaceutically acceptable salt thereof disclosed herein can be administered as the sole active ingredient or in combination with at least one second active ingredient.

The subject compounds are incorporated into pharmaceutical compositions or formulations. The compositions will contain pharmaceutically acceptable diluents and/or carriers, i. e. diluents or carriers that are physiologically compatible and substantially free from pathogenic impurities. Suitable excipients or carriers and methods for preparing administrable compositions are known or apparent to those skilled in the art and are described in more detail in such publications as Remington's Pharmaceutical Science, Mack Publishing Co, NJ (1991). The compositions may also be in the form of controlled release or sustained release compositions as known in the art. For many applications the subject compounds are administered for morning/daytime dosing, with off period at night.

The subject compounds may be used per se, or in the form of their pharmaceutically acceptable salts, such as hydrochlorides, hydrobromides, acetates, sulfates, citrates, carbonates, trifluoroacetates and the like. When compounds contain relatively acidic functionalities, salts can be obtained by addition of the desired base, either neat or in a suitable inert solvent. Examples of pharmaceutically acceptable base addition salts include sodium, potassium, calcium, ammonium, organic amino, or magnesium salts, or the like. When compounds contain relatively basic functionalities, salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al, "Pharmaceutical Salts", Journal of Pharmaceutical Science, 1977, 66, 1-19).

The neutral forms of the compounds may be regenerated by contacting the salt with a base or acid, and isolating the parent compound in the conventional manner. The parent form of the compound differs from the various salt forms in certain physical properties, such as solubility in polar solvents, but otherwise the salts are equivalent to the parent form of the compound for the purposes of this invention.

In addition to salt forms, this invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity.

Certain compounds of the invention can exist in unsolvated forms as well as solvated forms, including hydrated forms. In general, the solvated forms are equivalent to unsolvated forms and are intended to be encompassed within the scope of the present invention. Certain compounds of the invention may exist in multiple crystalline or amorphous forms. In general, all physical forms are equivalent for the uses contemplated by the present invention and are intended to be within the scope of the invention.

Some of the subject compounds possess asymmetric carbon atoms (optical centers) or double bonds; the racemates, diastereomers, geometric isomers and individual isomers are all intended to be encompassed within the scope of the present invention.

The compounds of the invention may also contain unnatural proportions of atomic isotopes at one or more of the atoms that constitute such compounds, such as deuterium, e.g. —$CD_3$, $CD_2H$ or $CDH_2$ in place of methyl. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

The compounds are generally administered in a "therapeutically effective amount", i.e. the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The contacting is generally effected by administering to the subject an effective amount of one or more compounds having the general formula I (supra), including the various embodiments described above. Generally administration is adjusted to achieve a therapeutic dosage of about 0.1 to 50, preferably 0.5 to 10, more preferably 1 to 10 mg/kg, though optimal dosages are compound specific, and generally empirically determined for each compound.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the mimetic is usually a minor component (from about 0.1 to about 50% by weight or preferably from about 1 to about 40% by weight) with the remainder being various vehicles or carriers and processing aids helpful for forming the desired dosing form. Unit dosage formulations are preferably about of 5, 10, 25, 50, 100, 250, 500, or 1,000 mg per unit. In a particular embodiment, unit dosage forms are packaged in a multipack adapted for sequential use, such as blisterpack comprising sheets of at least 6, 9 or 12 unit dosage forms.

The subject compositions may also be coformulated and/or coadministered with a different compound to treat programmed cell death.

TABLE 1

Active Compounds

1

2

3

4

5

TABLE 1-continued
Active Compounds
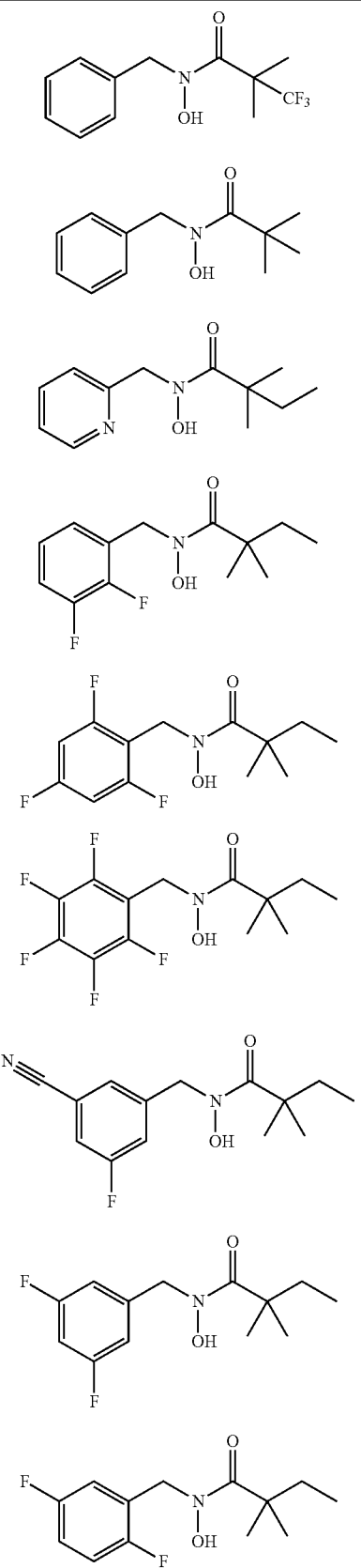
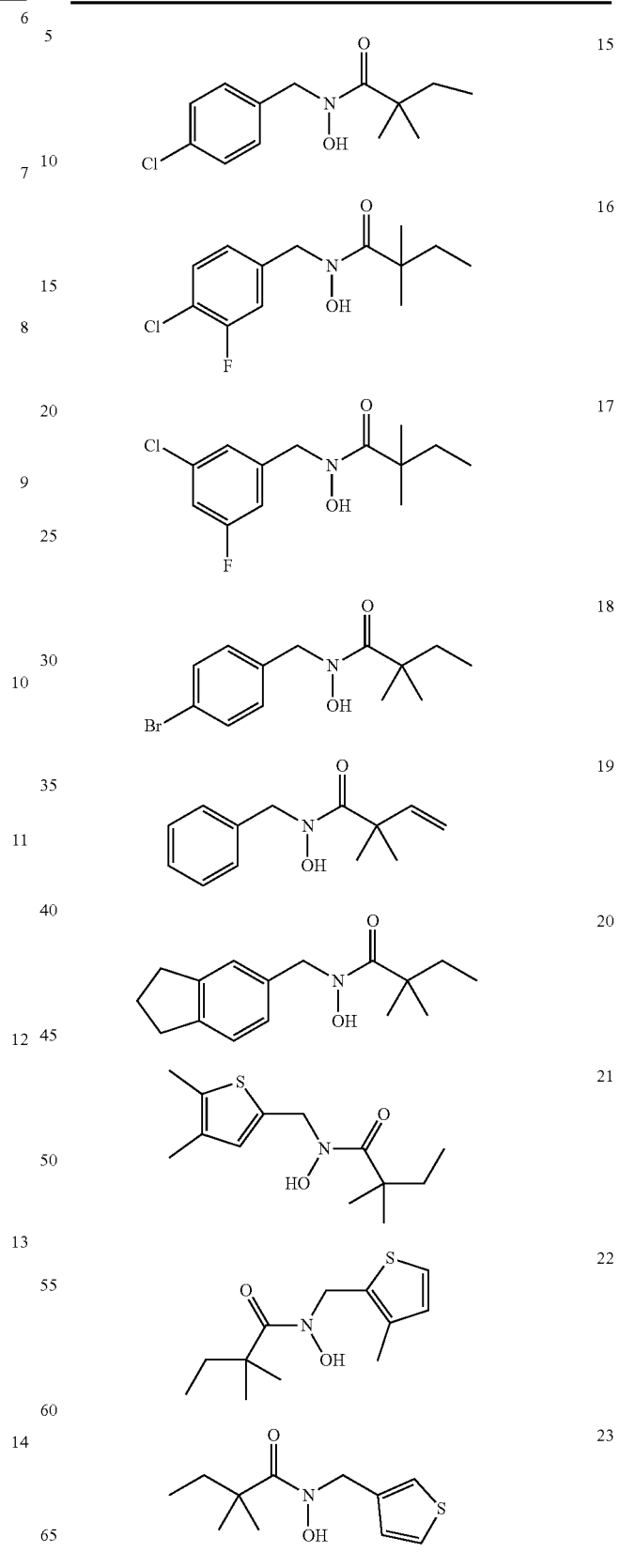

TABLE 1-continued
Active Compounds
| | |
|---|---|
| 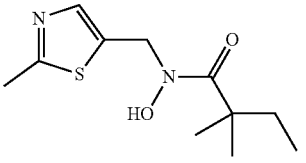 [SMILES: CCC(C)(C)C(=O)N(O)Cc1cnc(C)s1] | 24 |
| 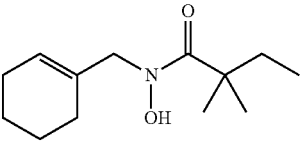 [SMILES: CCC(C)(C)C(=O)N(O)CC1=CCCCC1] | 25 |
| 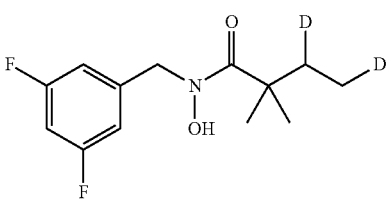 [SMILES: [2H]CC([2H])C(C)(C)C(=O)N(O)Cc1cc(F)cc(F)c1] | 26 |
| 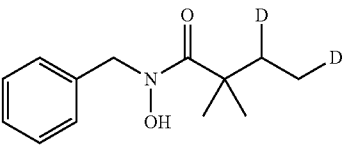 [SMILES: [2H]CC([2H])C(C)(C)C(=O)N(O)Cc1ccccc1] | 27 |
| 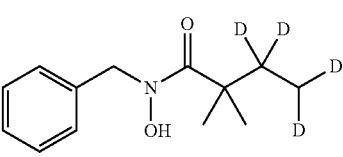 [SMILES: [2H]C([2H])C([2H])([2H])C(C)(C)C(=O)N(O)Cc1ccccc1] | 28 |
| 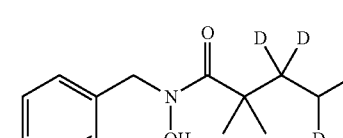 | 29 |
| 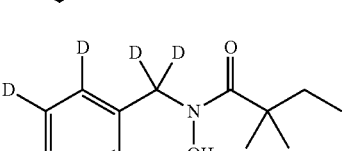 | 30 |
| 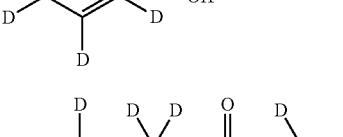 | 31 |
| 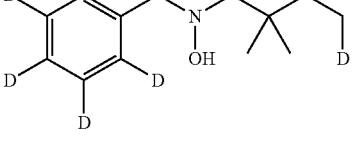 | 32 |
TABLE 1-continued
Active Compounds
| | |
|---|---|
| 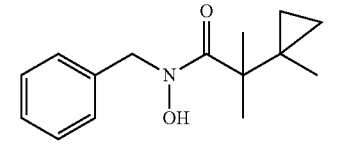 [SMILES: CC1(C(C)(C)C(=O)N(O)Cc2ccccc2)CC1] | 33 |
| 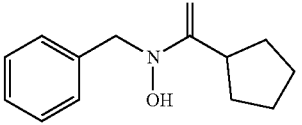 | 34 |
| 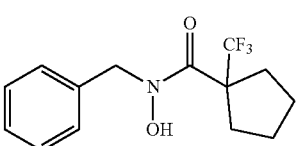 | 35 |
| 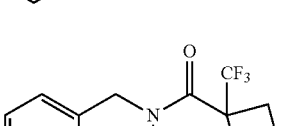 | 36 |
| 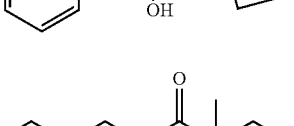 | 37 |
| 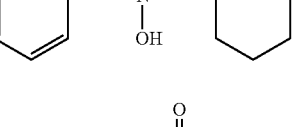 | 38 |
| 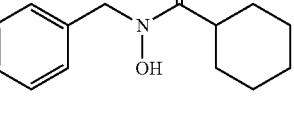 | 39 |
| 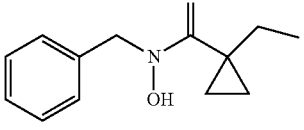 | 40 |
| 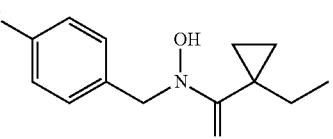 | 41 |

TABLE 1-continued

Active Compounds

| # | Structure |
|---|---|
| 42 | 4-Br-C6H4-CH2-N(OH)-C(O)-C(CH3)2-CF3 |
| 43 | 4-F-C6H4-CH2-N(OH)-C(O)-C(CH3)2-CF3 |
| 44 | 4-Cl-C6H4-CH2-N(OH)-C(O)-C(CH3)2-CF3 |
| 45 | 3,5-diF-C6H3-CH2-N(OH)-C(O)-C(CH3)2-CF3 |
| 46 | 3,4,5-triF-C6H2-CH2-N(OH)-C(O)-C(CH3)2-CF3 |
| 47 | (4,5-diMe-thien-2-yl)-CH2-N(OH)-C(O)-C(CH3)2-CF3 |
| 48 | (3-Me-thien-2-yl)-CH2-N(OH)-C(O)-C(CH3)2-CF3 |
| 49 | (thien-2-yl)-CH2-N(OH)-C(O)-C(CH3)2-CF3 |
| 74 | C6H5-CH2-N(OH)-C(O)-C(CH3)2-CHF2 |
| 75 | 3,5-diF-C6H3-CH2-N(OH)-C(O)-C(CH3)2-CHF2 |
| 76 | 3,5-diF-C6H3-CH2-N(OH)-C(O)-C(CH3)(CH2CH2F) |
| 84 | N-benzyl-1-(5-fluoropyrimidin-2-yl)-N-hydroxypiperidine-4-carboxamide |
| 85 | 1-(5-fluoropyrimidin-2-yl)-N-(4-fluorobenzyl)-N-hydroxypiperidine-4-carboxamide |
| 86 | N-(3,5-difluorobenzyl)-1-(5-fluoropyrimidin-2-yl)-N-hydroxypiperidine-4-carboxamide |

Necrosis Inhibitory Activity

| # | EC$_{50}$ |
|---|---|
| 1 | 1-1000 nM |
| 2 | 1-1000 nM |
| 3 | 1-1000 nM |
| 4 | 1-1000 nM |
| 5 | 1-1000 nM |
| 6 | 1-1000 nM |
| 7 | 1-1000 nM |
| 8 | 1-10 uM |
| 9 | 1-1000 nM |
| 10 | 1-10 uM |
| 11 | 1-10 uM |
| 12 | 1-1000 nM |
| 13 | 1-1000 nM |

-continued
| # | EC$_{50}$ |
|---|---|
| 14 | 1-1000 nM |
| 15 | 1-1000 nM |
| 16 | 1-1000 nM |
| 17 | 1-1000 nM |
| 18 | 1-1000 nM |
| 19 | 1-1000 nM |
| 20 | 1-1000 nM |
| 21 | 1-1000 nM |
| 22 | 1-10 uM |
| 23 | 1-1000 nM |
| 24 | 1-1000 nM |
| 25 | 1-1000 nM |
| 26 | 1-1000 nM |
| 27 | 1-1000 nM |
| 28 | 1-1000 nM |
| 29 | 1-1000 nM |
| 30 | 1-1000 nM |
| 31 | 1-1000 nM |
| 32 | 1-1000 nM |
| 33 | 1-10 uM |
| 34 | 1-1000 nM |
| 35 | 1-1000 nM |
| 36 | 1-1000 nM |
| 37 | 1-10 uM |
| 38 | 1-10 uM |
| 39 | 1-100 uM |
| 40 | 1-10 uM |
| 41 | 1-10 uM |
| 42 | 1-1000 nM |
| 43 | 1-1000 nM |
| 44 | 1-1000 nM |
| 45 | 1-1000 nM |
| 46 | 1-10 uM |
| 47 | 1-1000 nM |
| 48 | 1-10 uM |
| 49 | 1-1000 nM |
| 74 | 1-1000 nM |
| 75 | 1-1000 nM |
| 76 | 1-10 uM |
| 84 | 1-1000 nM |
| 85 | 1-10 uM |
| 86 | 1-1000 nM |
Ferroptosis Inhibitor Activity 1 Um Threshold Activity Extrapolated
| # | EC$_{50}$ |
|---|---|
| 1 | 1-10 uM |
| 2 | 1-10 uM |
| 3 | 1-10 uM |
| 4 | 1-10 uM |
| 5 | 1-10 uM |
| 6 | 1-10 uM |
| 7 | 1-10 uM |
| 8 | 1-10 uM |
| 9 | 1-10 uM |
| 10 | 1-10 uM |
| 11 | 1-10 uM |
| 12 | 1-10 uM |
| 13 | 1-10 uM |
| 14 | 1-10 uM |
| 15 | 1-10 uM |
| 16 | 1-10 uM |
| 17 | 1-10 uM |
| 18 | 1-10 uM |
| 19 | 1-10 uM |
| 20 | 1-10 uM |
| 21 | 1-10 uM |
| 22 | 1-10 uM |
| 23 | 1-10 uM |
| 24 | 1-10 uM |
| 25 | 1-10 uM |
| 26 | 1-10 uM |
| 27 | 1-10 uM |
| 28 | 1-10 uM |
| 29 | 1-10 uM |
| 30 | 1-10 uM |
| 31 | 1-10 uM |
| 32 | 1-10 uM |
| 33 | 1-10 uM |
| 34 | 1-10 uM |
| 35 | 1-10 uM |
| 36 | 1-10 uM |
| 37 | 1-10 uM |
| 38 | 1-10 uM |
| 39 | 1-10 uM |
| 40 | 1-10 uM |
| 41 | 1-10 uM |
| 42 | 1-10 uM |
| 43 | 1-10 uM |
| 44 | 1-10 uM |
| 45 | 1-10 uM |
| 46 | 1-10 uM |
| 47 | 1-10 uM |
| 48 | 1-10 uM |
| 49 | 1-10 uM |
| 74 | 1-10 uM |
| 75 | 1-10 uM |
| 76 | 1-10 uM |
| 84 | 1-10 uM |
| 85 | 1-10 uM |
| 86 | 1-10 uM |
TABLE 2
Active Pro-drugs
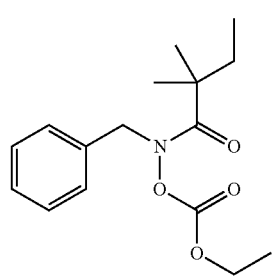 [SMILES: CCOC(=O)ON(Cc1ccccc1)C(=O)C(C)(C)CC]
50

TABLE 2-continued
Active Pro-drugs
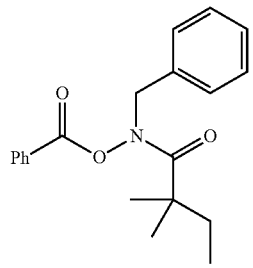 [SMILES: CCC(C)(C)C(=O)N(Cc1ccccc1)OC(=O)c1ccccc1]
51
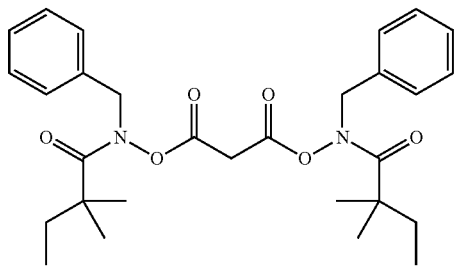 [SMILES: CCC(C)(C)C(=O)N(Cc1ccccc1)OC(=O)CC(=O)ON(Cc1ccccc1)C(=O)C(C)(C)CC]
52
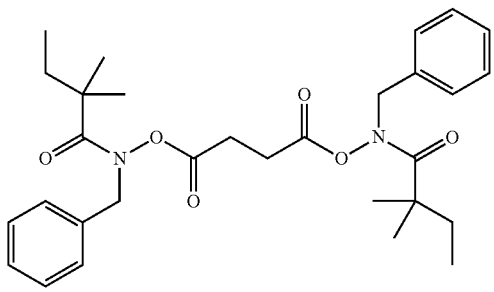 [SMILES: CCC(C)(C)C(=O)N(Cc1ccccc1)OC(=O)CCC(=O)ON(Cc1ccccc1)C(=O)C(C)(C)CC]
53
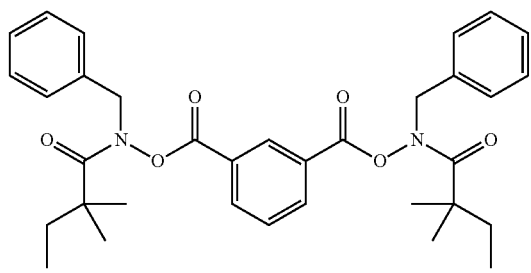 [SMILES: CCC(C)(C)C(=O)N(Cc1ccccc1)OC(=O)c1cccc(C(=O)ON(Cc2ccccc2)C(=O)C(C)(C)CC)c1]
54
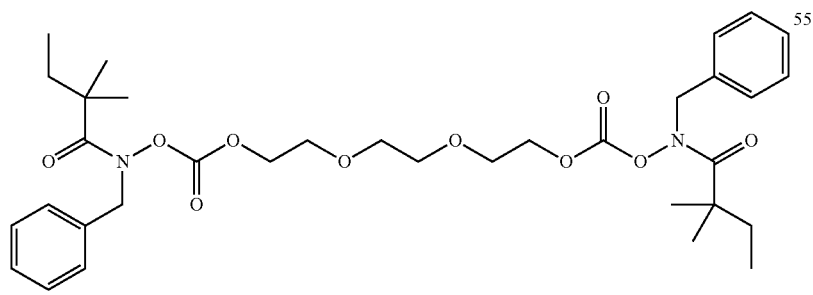
55

TABLE 2-continued
Active Pro-drugs
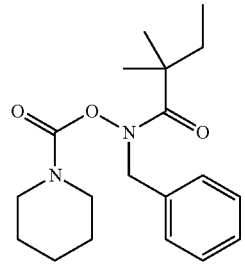 [SMILES: CCC(C)(C)C(=O)N(Cc1ccccc1)OC(=O)N1CCCCC1]
56
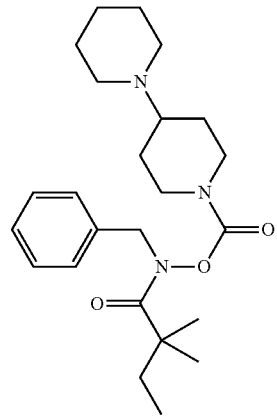 [SMILES: CCC(C)(C)C(=O)N(Cc1ccccc1)OC(=O)N1CCC(N2CCCCC2)CC1]
57
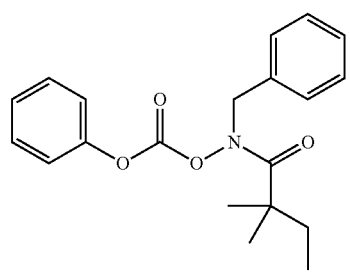 [SMILES: CCC(C)(C)C(=O)N(Cc1ccccc1)OC(=O)Oc1ccccc1]
58
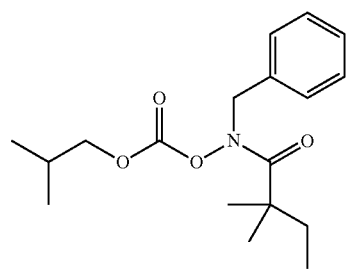 [SMILES: CCC(C)(C)C(=O)N(Cc1ccccc1)OC(=O)OCC(C)C]
59
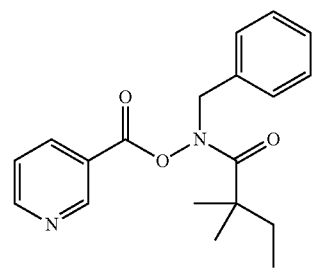 [SMILES: CCC(C)(C)C(=O)N(Cc1ccccc1)OC(=O)c1cccnc1]
60

TABLE 2-continued
Active Pro-drugs
61
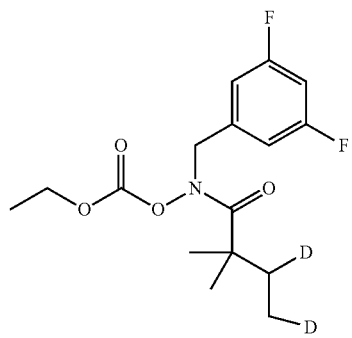 [SMILES: [2H]CC([2H])C(C)(C)C(=O)N(Cc1cc(F)cc(F)c1)OC(=O)OCC]
62
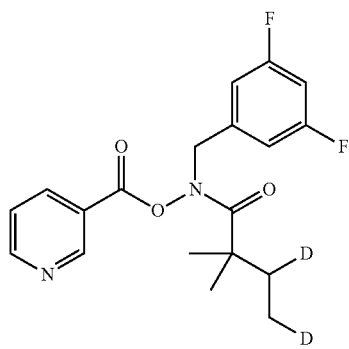 [SMILES: [2H]CC([2H])C(C)(C)C(=O)N(Cc1cc(F)cc(F)c1)OC(=O)c1cccnc1]
63
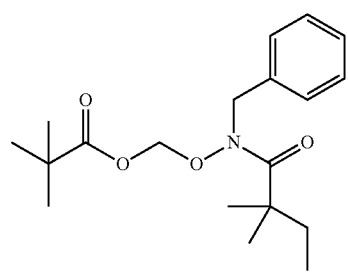 [SMILES: CCC(C)(C)C(=O)N(Cc1ccccc1)OCOC(=O)C(C)(C)C]
64
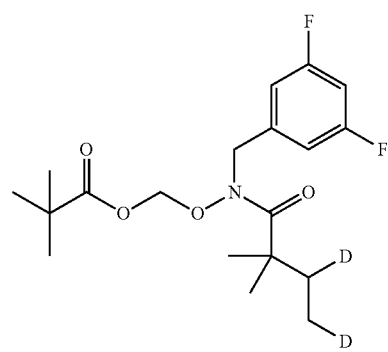 [SMILES: [2H]CC([2H])C(C)(C)C(=O)N(Cc1cc(F)cc(F)c1)OCOC(=O)C(C)(C)C]

TABLE 2-continued

Active Pro-drugs

| | |
|---|---|
| 65 | [Structure: 2-methoxyethyl carbonate linked via O-N to amide of 3,5-difluorobenzyl with 2,2-dimethyl-3-deuteriomethyl-3-deuterio group] |
| 66 | [Structure: MeO-(CH$_2$CH$_2$O)$_2$-carbonate-O-N(3,5-difluorobenzyl)-C(O)-C(CH$_3$)$_2$-CHD-CH$_2$D] |
| 67 | [Structure: MeO-(CH$_2$CH$_2$O)$_3$-carbonate-O-N(3,5-difluorobenzyl)-C(O)-C(CH$_3$)$_2$-CHD-CH$_2$D] |
| 68 | [Cyclic phosphoramidate structure with benzyl, ethyl, dimethyl, and N(CH$_3$)$_2$ groups] |
| 69 | [Structure: N-benzyl-2,2-dimethylbutanoyl-N-O-CH$_2$-O-P(O)(OCH$_2$Ph)$_2$] |

TABLE 2-continued
Active Pro-drugs
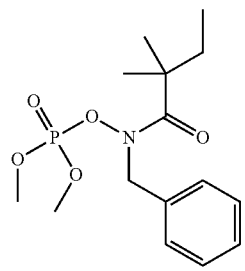 [SMILES: CCC(C)(C)C(=O)N(Cc1ccccc1)OP(=O)(OC)OC]
70
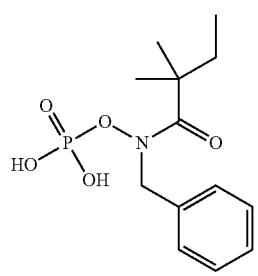 [SMILES: CCC(C)(C)C(=O)N(Cc1ccccc1)OP(=O)(O)O]
71
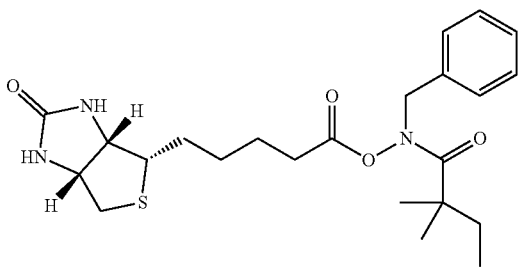 [SMILES: CCC(C)(C)C(=O)N(Cc1ccccc1)OC(=O)CCCC[C@@H]1SC[C@@H]2NC(=O)N[C@@H]21]
72
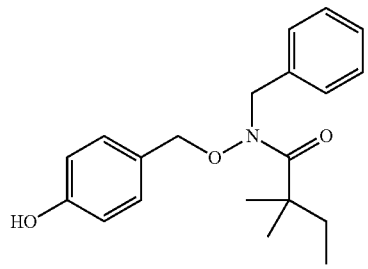 [SMILES: CCC(C)(C)C(=O)N(Cc1ccccc1)OCc1ccc(O)cc1]
73
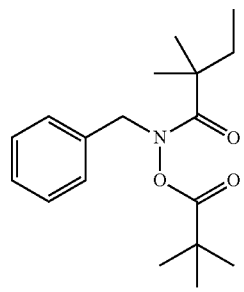 [SMILES: CCC(C)(C)C(=O)N(Cc1ccccc1)OC(=O)C(C)(C)C]
77

TABLE 2-continued
Active Pro-drugs
79
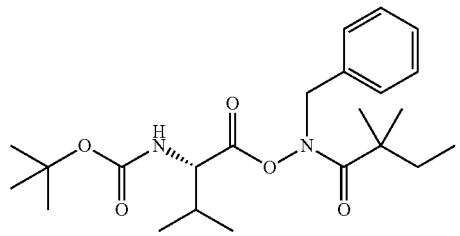 [SMILES: CCC(C)(C)C(=O)N(Cc1ccccc1)OC(=O)[C@@H](NC(=O)OC(C)(C)C)C(C)C]
80
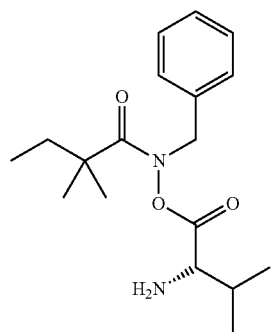
81
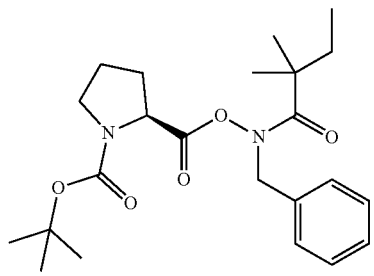 [SMILES: CCC(C)(C)C(=O)N(Cc1ccccc1)OC(=O)[C@@H]1CCCN1C(=O)OC(C)(C)C]
82
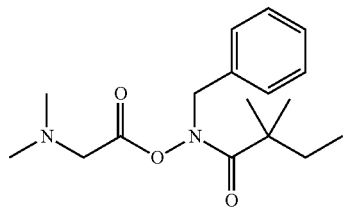 [SMILES: CCC(C)(C)C(=O)N(Cc1ccccc1)OC(=O)CN(C)C]
83
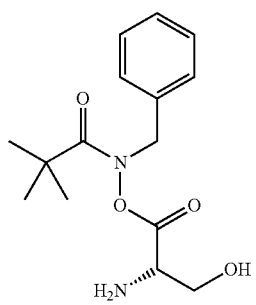

TABLE 2-continued

Active Pro-drugs

87

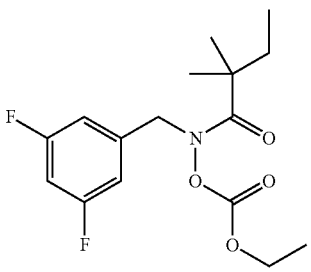 [SMILES: CCOC(=O)ON(Cc1cc(F)cc(F)c1)C(=O)C(C)(C)CC]

TABLE 2

Active Pro-drugs

| Compound | EC50(nM) | | |
|---|---|---|---|
| 50 | 69.62 | 65 | 37.2 |
| 51 | 283.8 | 66 | 46.0 |
| 52 | 42.23 | 67 | 58.5 |
| 53 | 85.5 | 68 | 1620 |
| 54 | 465.7 | 69 | weak |
| 55 | 99.29 | 70 | 1695 |
| 56 | weak | 71 | 28.71 |
| 57 | weak | 72 | 159,3 |
| 58 | 45.1 | 73 | 489 |
| 59 | 44.8 | 77 | 6832 |
| 60 | 83.5 | 79 | 1432 |
| 61 | 127.5 | 80 | 24.24 |
| 62 | 45.3 | 81 | 3252 |
| 63 | 62.9 | 82 | 115.5 |
| 64 | 91.4 | 83 | 898 |
| | | 87 | 67.8 |

Prodrug Enhanced Metabolic Stability: Liver Microsome (L), Hepatocyte (H) and PK

| # | L | H | PK |
|---|---|---|---|
| 50 | + | + | + |
| 51 | + | + | + |
| 52 | + | + | + |
| 53 | + | + | + |
| 54 | + | + | + |
| 55 | + | + | + |
| 56 | + | + | + |
| 57 | + | + | + |
| 58 | + | + | + |
| 59 | + | + | + |
| 60 | + | + | + |
| 61 | + | + | + |
| 62 | + | + | + |
| 63 | + | + | + |
| 64 | + | + | + |
| 65 | + | + | + |
| 66 | + | + | + |
| 67 | + | + | + |
| 68 | + | + | + |
| 69 | + | + | + |
| 70 | + | + | + |
| 71 | + | + | + |
| 72 | + | + | + |
| 73 | + | + | + |
| 74 | + | + | + |
| 75 | + | + | + |
| 76 | + | + | + |
| 77 | + | + | + |
| 78 | + | + | + |
| 79 | + | + | + |
| 80 | + | + | + |
| 81 | + | + | + |
| 82 | + | + | + |
| 83 | + | + | + |
| 87 | + | + | + |

Representative Metabolic Stability Data I; +, Extrapolated.

| | liver microsome stability | | | | | |
|---|---|---|---|---|---|---|
| Compd | Human $T_{1/2}$ (min) | Rat $T_{1/2}$ (min) | Mouse $T_{1/2}$ (min) | Dog $T_{1/2}$ (min) | mini-pig $T_{1/2}$ (min) | Monkey $T_{1/2}$ (min) |
| 92 | 204.0 | 25.15 | 32.45 | 7.1 | 53.5 | 2.95 |
| 13 | 228 | 19.9 | 17.1 | 2.34 | + | 4.72 |
| 15 | 96.75 | 41.10 | 16.56 | + | + | + |
| 27 | 178.30 | 19.79 | 26.53 | 1.5 | + | 0.6 |
| 28 | 195.49 | 28.61 | 33.61 | 3.5 | + | 3.3 |
| 26 | 136 | 23.3 | 21.1 | 2.31 | + | 4.97 |
| 19 | 153.59 | 28.86 | 25.38 | 6.0 | + | 0.3 |

Representative Metabolic Stability Data II, +, Extrapolated.

| | Hepatocyte stability | | | | | |
|---|---|---|---|---|---|---|
| Compd | Human $T_{1/2}$ (min) | Rat $T_{1/2}$ (min) | Mouse $T_{1/2}$ (min) | Dog $T_{1/2}$ (min) | mini-pig $T_{1/2}$ (min) | Monkey $T_{1/2}$ (min) |
| 92 | 73.1 | 14.2 | 24.4 | 13.9 | 23.1 | 18.9 |
| 13 | 152 | 28 | 20.1 | 12.8 | 21.2 | 24.9 |
| 15 | + | + | + | + | + | + |
| 27 | + | + | + | + | + | + |
| 28 | + | + | + | + | + | + |
| 26 | 109.6 | 33.36 | 20.98 | 8.43 | ND | 19.33 |
| 19 | + | + | + | + | + | + |

Representative PK Date of Pro-Drug Compounds

| | SD rat. PO-10 mg/kg | | |
|---|---|---|---|
| ID | $t_{1/2}$ (h) | AUC$_{tot}$ (ng · h/ml) | F (%) |
| 92 | 0.64 | 29.9 | 1.15 |
| 13 | 1.17$^a$ | 7525$^a$ | 62.8$^a$ |
| 15 | 4,884 | 923 | 20.3 |
| 27 | 0.92 | 78.6 | 5.29 |

| | SD rat. PO-10 mg/kg | | |
|---|---|---|---|
| ID | $t_{1/2}$ (h) | $AUC_{tot}$ (ng · h/ml) | F (%) |
| 28 | 0.617 | 318 | 14.8 |
| 26 | 2.85[a] | 8341[a] | 74.1[a] |

Note:
[a] dose 60 mg/Kg micropower,

Representative PK Date of Pro-Drug Compounds

| | | | po, 10 mg/mL | |
|---|---|---|---|---|
| Cmpd | Species | Formulation | $AUC_{tot}$ (ng · h/ml) | F (%) |
| 50 | Rat | Bile duct cannulation (BDC) | 380 | 13.5 |
| 60 | Rat | Bile duct cannulation (BDC) | 421 | 23.9 |
| 63 | Rat | Bile duct cannulation (BDC) | 443 | 25.8 |
| 61 | Rat | Bile duct cannulation (BDC) | 2393 | 163 |
| 62 | Rat | Bile duct cannulation (BDC) | 1378 | 103 |
| 64 | Rat | Bile duct cannulation (BDC) | 1342 | 71.6 |
| 65 | Rat | Bile duct cannulation (BDC) | 1147 | 61.2 |
| 87 | Rat | Bile duct cannulation (BDC) | 1783 | 85 |

Representative IC50 of hRIP1 Kinase Assay Correlated with Our IC50 of Cell Necrosis Assay:

| Compound No | Cell viability assay, EC50 (nM) | Human RIP1 kinase assay, IC50(nM) |
|---|---|---|
| 13 | <100 nM | <100 nM |
| 35 | 1-1000 nM | 100-1000 nM |
| 20 | <100 nM | <100 nM |
| 38 | 1-10000 nM | 100-1000 nM |
| 84 | <100 nM | <100 nM |
| 86 | 1-1000 nM | <100 nM |
| 24 | 1-1000 nM | 100-1000 nM |
| 48 | 1-10000 nM | 100-1000 nM |
| 23 | 1-1000 nM | <100 nM |
| 16 | 1-1000 nM | <100 nM |

Synthesis

Compound 1: Preparation of N-(2-fluorobenzyl)-N-hydroxy-2,2-dimethylbutanamide

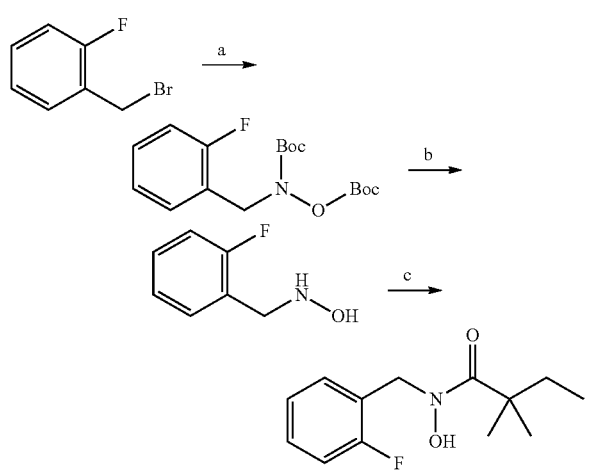

Reagent and conditions; (a) tert-butyl (tert-butoxycarbonyl)oxycarbamate, 1N NaOH, TBAB, DCM; (b) TFA, DCM; (c) 2,2-dimethylbutanoyl chloride, aq. NaHCO$_3$, THF, H$_2$O.

Tert-butyl (tert-butoxycarbonyl)oxycarbamate (70 mg) and 1-(bromomethyl)-2-fluorobenzene (56.7 mg) were dissolved in CH$_2$Cl$_2$ (7 ml). The mixture was added 1M NaOH (0.33 ml) and tetrabutylammonium bromide (4.83 mg), and stirred at room temperature for overnight. The resulting mixture was washed with water and dried with Na$_2$SO$_4$, concentrated in vacuo and purification by silica gel chromatography to give tert-butyl ((tert-butoxycarbonyl)oxy)(2-fluorobenzyl)carbamate (82 mg, 80%). $^1$HNMR (400 MHz, CDCl$_3$): δ 7.31-7.37 (m, 4H), 4.52 (s, 2H), 1.46 (s, 9H), 1.44 (s, 9H).

The above intermediate was dissolved in CH$_2$Cl$_2$ (2 ml), TFA (0.5 ml) was added at 0° C. The mixture was stirred at room temperature for 2 h and concentrated to give N-(2-fluorobenzyl)hydroxylamine (80 mg) as a TFA salt, which was used for next step without further purification.

The above intermediate was dissolved in THF (3 ml) and water (3 ml) and 1 ml of saturated aqueous NaHCO$_3$ was added. The mixture was stirred at room temperature for 30 min, then cooled to 0° C., 2,2-dimethylbutanoylchloride (40 mg) was added and stirred for overnight. The mixture was extracted with EtOAc, washed with brine, dried (Na$_2$SO4), and concentrated in vacuo. Purification by silica gel chromatography to give compound 1 (32 mg, total yield 45%). $^1$HNMR (400 MHz, CDCl$_3$): δ 7.34 (td, J=7.7, 1.8 Hz, 1H), 7.30-7.25 (m, 1H), 7.12 (td, J=7.5, 1.1 Hz, 1H), 7.09-7.03 (m, 1H), 4.96 (s, 2H), 1.66 (q, J=7.5 Hz, 2H), 1.24 (s, 7H), 0.83 (t, J=7.5 Hz, 3H). LC-MS (m/z) 240.3 (M+H$^+$)

Compound 2: N-(3-fluorobenzyl)-N-hydroxy-2,2-dimethylbutanamide

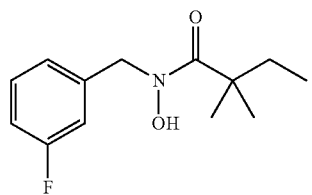 [SMILES: CCC(C)(C)C(=O)N(O)Cc1cccc(F)c1]

The titled compound 2 was prepared in 35% yield from tert-butyl (tert-butoxycarbonyl)oxycarbamate (70 mg), 1-(bromomethyl)-3-fluorobenzene (56.7 mg) and 2,2-dimethylbutanoylchloride (40.2 mg) according to the procedure outlined for compound 1. 1H NMR (400 MHz, CDCl$_3$) δ 7.34-7.27 (m, 1H), 7.07 (d, J=7.5 Hz, 1H), 7.02-6.96 (m, 2H), 4.87 (s, 2H), 1.67 (q, J=7.5 Hz, 2H), 1.25 (s, 6H), 0.85 (t, J=7.5 Hz, 3H). LC-MS (m/z) 240.4 (M+H$^+$).

Compound 3: N-(2-chlorobenzyl)-N-hydroxy-2,2-dimethylbutanamide

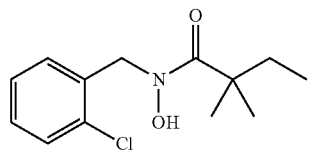 [SMILES: CCC(C)(C)C(=O)N(O)Cc1ccccc1Cl]

The titled compound 3 was prepared in 33% yield from tert-butyl (tert-butoxycarbonyl)oxycarbamate (70 mg), 1-(bromomethyl)-2-chlorobenzene (61.5 mg) and 2,2-dimethylbutanoylchloride (40.2 mg) according to the procedure outlined for compound 1. 1H NMR (400 MHz, CDCl$_3$) δ 7.36 (dd, J=7.3, 1.9 Hz, 1H), 7.33 (dd, J=7.3, 2.0 Hz, 1H), 7.28-7.22 (m, 2H), 5.01 (s, 2H), 1.65 (q, J=7.5 Hz, 2H), 1.23 (s, 6H), 0.85 (t, J=7.5 Hz, 3H). LC-MS (m/z) 256.4 (M+H$^+$).

Compound 4: N-(3-chlorobenzyl)-N-hydroxy-2,2-dimethylbutanamide

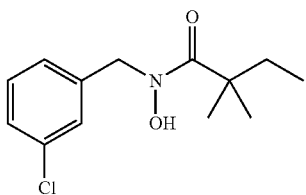 [SMILES: CCC(C)(C)C(=O)N(O)Cc1cccc(Cl)c1]

The titled compound 4 was prepared in 30% yield from tert-butyl (tert-butoxycarbonyl)oxycarbamate (70 mg), 1-(bromomethyl)-3-chlorobenzene (61.5 mg) and 2,2-dimethylbutanoylchloride (40.2 mg) according to the procedure outlined for compound 1. $^1$H NMR (400 MHz, CDCl$_3$) δ 7.30-7.26 (m, 3H), 7.19-7.16 (m, 1H), 4.85 (s, 2H), 1.67 (q, J=7.5 Hz, 2H), 1.25 (s, 6H), 0.84 (t, J=7.5 Hz, 3H). LC-MS (m/z) 256.3 (M+H$^+$)

Compound 5: N-(3-bromobenzyl)-N-hydroxy-2,2-dimethylbutanamide

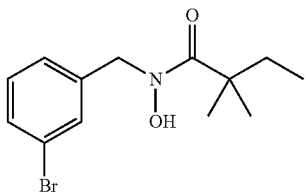 [SMILES: CCC(C)(C)C(=O)N(O)Cc1cccc(Br)c1]

The titled compound 5 was prepared in 30% yield from tert-butyl (tert-butoxycarbonyl)oxycarbamate (70 mg), 1-bromo-3-(bromomethyl)benzene (75 mg) and 2,2-dimethylbutanoylchloride (40.2 mg) according to the procedure outlined for compound 1. 1H NMR (400 MHz, CDCl$_3$) δ 7.46-7.40 (m, 2H), 7.23-7.19 (m, 2H), 4.83 (s, 2H), 1.67 (q, J=7.5 Hz, 2H), 1.24 (s, 6H), 0.84 (t, J=7.5 Hz, 3H). LC-MS (m/z) 300.2, 302.4 (M+H$^+$)

Compound 6: N-benzyl-3,3,3-trifluoro-N-hydroxy-2,2-dimethylpropanamide

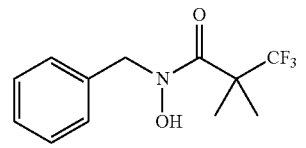 [SMILES: CC(C)(C(=O)N(O)Cc1ccccc1)C(F)(F)F]

A mixture of n-benzylhydroxylamine hydrochloride (81.8 mg), 3,3,3-trifluoro-2,2-dimethylpropanoic acid (80 mg) and N-(3-Dimethylaminopropyl)-N'-ethylcarbodiimide hydrochloride (147.2 mg) were dissolved in dry DMF (2 mL), and 0.27 mL of DIEA was added. The reaction mixtures were stirred at room temperature for overnight. The mixture was extracted with EtOAc, washed with water and brine, dried (Na$_2$SO4), and concentrated in vacuo. Purification by silica gel chromatography to give compound 6. 1H NMR (400 MHz, CDCl$_3$) δ 7.38-7.32 (m, 3H), 7.30-7.27 (m, 2H), 4.89 (s, 2H), 1.54 (s, 6H). LC-MS (m/z) 262.2 (M+H$^+$)

Compound 7: N-benzyl-N-hydroxypivalamide

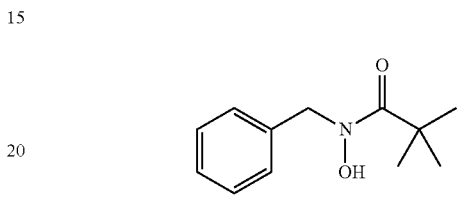

n-benzylhydroxylamine hydrochloride (50 mg) was dissolved in 1 ml of THF/H$_2$O (1:1) and 0.25 ml of saturated aqueous NaHCO$_3$. The solution was cooled to 0° C. and pivaloyl chloride (37.5 mg) was added and the mixture was stirred at room temperature for 16 h. The mixture was extracted with EtOAc and the combined organic layer washed with brine, dried (Na$_2$SO4) and concentrated in vacuo. Purification by pre-TLC to give compound 7 (130 mg, 46%) as an white solid. 1H NMR (400 MHz, CDCl$_3$) δ 7.40-7.32 (m, 3H), 7.31-7.29 (m, 2H), 4.93 (s, 2H), 1.33-1.31 (m, 9H). LC-MS (m/z) 208.3 (M+H$^+$)

Compound 8: N-hydroxy-2,2-dimethyl-N-(pyridin-2-ylmethyl)butanamide

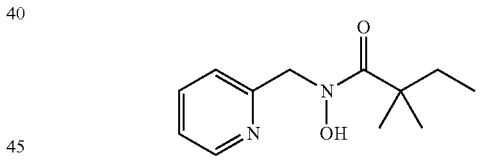

The titled compound 8 was prepared in 31% yield from tert-butyl (tert-butoxycarbonyl)oxycarbamate (119 mg), 2-(bromomethyl)pyridine (88 mg) and 2,2-dimethylbutanoylchloride (68 mg) according to the procedure outlined for compound 1. $^1$HNMR (400 MHz, CDCl$_3$) δ 8.38 (d, J=4.6 Hz, 1H), 7.75-7.65 (m, 1H), 7.31 (d, J=7.8 Hz, 1H), 7.24-7.16 (m, 1H), 4.97 (s, 2H), 1.78 (q, J=7.5 Hz, 2H), 1.27 (s, 6H), 0.84 (t, J=7.5 Hz, 3H). LC-MS (m/z) 223.5 (M+H$^+$).

Compound 9: N-(2,3-difluorobenzyl)-N-hydroxy-2,2-dimethylbutanamide

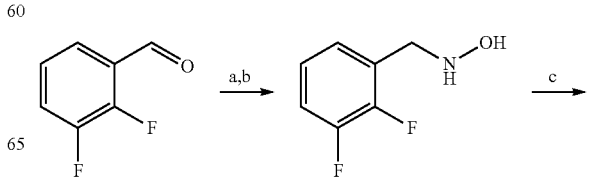

-continued

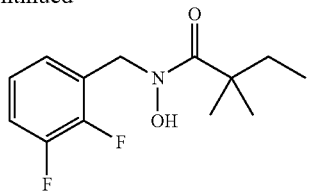

Reagent and conditions: (a): NH₂OH*HCl; Na₂CO₃; (b): BH₃ Py; (c) 2,2-dimethylbutanoyl chloride, NaHCO₃, THF/H₂O, 0° C. 30 min, rt, 16 h.

2,3-difluorobenzaldehyde (400 mg, 2.81 mmol) and hydroxylamine hydrochloride (215.15 mg, 3.10 mmol, 1.1 equiv) was stirred at room temperature in a mixture solution (THF/EtOH/H₂O, 4/10/2 mL) for 16 h. The mixture was extracted with EtOAc, washed with water and brine, dried (Na₂SO₄), and concentrated in vacuo to give (E)-2,3-difluorobenzaldehyde oxime as a white solid was used for next step without further purification (400 mg). $^1$H NMR (400 MHz, CDCl₃) δ 8.34 (s, 1H), 7.52-7.47 (m, 1H), 7.22-7.13 (m, 1H), 7.08 (tdd, J=8.0, 4.8, 1.5 Hz, 1H).

A mixture of (E)-2,3-difluorobenzaldehyde oxime (400 mg) and 8M pyridine-borane complex (0.64 mL) in 5 ml EtOH and 2 mL THF, and kept below 5° C. 10% HCl (6.5 mL) was added dropwise. The mixture then warmed up with 30 min to room temperature. The mixture was neutralized with Na₂CO₃, extracted with EtOAc, washed with water and brine, dried (Na₂SO₄), and concentrated in vacuo to give crude product N-(2,3-difluorobenzyl)hydroxylamine (310 mg), which was used directly in the next step without purification.

N-(2,3-difluorobenzyl)hydroxylamine (100 mg) was dissolved in 2 mL of THF/H₂O (1:1) and 0.44 ml of saturated aqueous NaHCO₃. The solution was cooled to 0° C. and 2,2-dimethylbutanoylchloride (92 mg) was added and the mixture was stirred at room temperature for 16 h. The mixture was extracted with EtOAc and the combined organic layer washed with brine, dried (Na₂SO₄) and concentrated in vacuo. Purification by silica gel chromatography to give compound 9. $^1$H NMR (400 MHz, CDCl₃) δ 7.03-7.13 (m, 3H), 4.96 (s, 2H), 1.67 (q, J=7.5 Hz, 3H), 1.24 (s, 6H), 0.83 (t, J=7.5 Hz, 3H). LC-MS (m/z) 258.3 (M+H⁺).

Compound 10: N-hydroxy-2,2-dimethyl-N-(2,4,6-trifluorobenzyl)butanamide

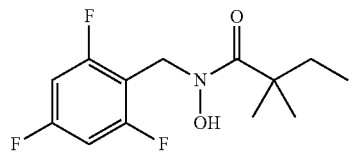 [SMILES: CCC(C)(C)C(=O)N(O)Cc1c(F)cc(F)cc1F]

The titled compound 10 was prepared in 30% yield from 2,4,6-trifluorobenzaldehyde (400 mg), hydroxylamine hydrochloride (191 mg), 8M pyridine-borane complex (0.625 mL) and 2,2-dimethylbutanoylchloride (125 mg) according to the procedure outlined for compound 9. $^1$HNMR (400 MHz, CDCl₃): δ 6.61-6.69 (m, 2H), 4.96 (s, 2H), 1.67 (q, J=7.5 Hz, 3H), 1.24 (s, 6H), 0.83 (t, J=7.5 Hz, 3H). LC-MS (m/z) 276.3 (M+H⁺).

Compound 11: N-hydroxy-2,2-dimethyl-N-((perfluorophenyl)methyl)butanamide

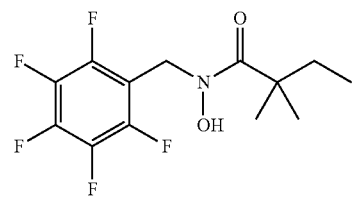 [SMILES: CCC(C)(C)C(=O)N(O)Cc1c(F)c(F)c(F)c(F)c1F]

The titled compound 11 was prepared in 33% yield from 2,3,4,5,6-pentafluorobenzaldehyde (400 mg), hydroxylamine hydrochloride (156 mg), 8M pyridine-borane complex (0.5 mL) and 2,2-dimethylbutanoylchloride (35 mg) according to the procedure outlined for compound 9. $^1$H NMR (400 MHz, CDCl₃) δ (ppm): 4.97 (s, 2H), 1.70 (q, J=7.6 Hz, 2H), 1.26 (s, 6H), 0.84 (t, J=7.6 Hz, 3H). LC-MS (m/z) 312.3 (M+H⁺).

Compound 12: N-(3-cyano-5-fluorobenzyl)-N-hydroxy-2,2-dimethylbutanamide

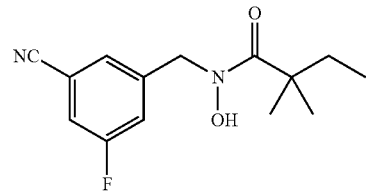 [SMILES: CCC(C)(C)C(=O)N(O)Cc1cc(F)cc(C#N)c1]

The titled compound 12 was prepared in 33% yield from 3-fluoro-5-formylbenzonitrile (400 mg), hydroxylamine hydrochloride (232 mg), 8M pyridine-borane complex (0.6 mL) and 2,2-dimethylbutanoylchloride (353 mg) according to the procedure outlined for compound 9. $^1$H NMR (400 MHz, CDCl₃) δ (ppm): 7.43 (s, 1H), 7.29-7.32 (m, 2H), 4.89 (s, 2H), 1.69 (q, J=7.6 Hz, 2H), 1.27 (s, 6H), 0.85 (t, J=7.6 Hz, 3H). LC-MS (m/z) 265.4 (M+H⁺).

Compound 13: N-(3,5-difluorobenzyl)-N-hydroxy-2,2-dimethylbutanamide

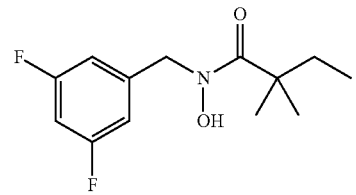 [SMILES: CCC(C)(C)C(=O)N(O)Cc1cc(F)cc(F)c1]

The titled compound 13 was prepared in 43% yield from 3,5-difluorobenzaldehyde (400 mg), hydroxylamine hydrochloride (215.3 mg), 8M pyridine-borane complex (0.7 mL) and 2,2-dimethylbutanoylchloride (360 mg) according to the procedure outlined for compound 9. $^1$H NMR (400 MHz, DMSO) δ 9.76 (s, 1H), 7.09 (td, J=9.4, 2.1 Hz, 1H), 6.95-6.86 (m, 2H), 4.66 (s, 2H), 1.64 (q, J=7.5 Hz, 2H), 1.13 (s, 6H), 0.72 (t, J=7.5 Hz, 3H). LC-MS (m/z) 258.4 (M+H⁺).

Compound 14: N-(2,5-difluorobenzyl)-N-hydroxy-2,2-dimethylbutanamide

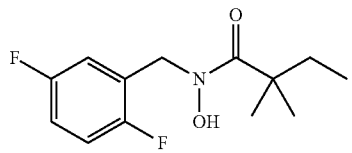 [SMILES: CCC(C)(C)C(=O)N(O)Cc1cc(F)ccc1F]

The titled compound was prepared in 43% yield from 2,5-difluorobenzaldehyde (400 mg), hydroxylamine hydrochloride (215.3 mg), 8M pyridine-borane complex (0.7 mL) and 2,2-dimethylbutanoylchloride (223 mg) according to the procedure outlined for compound 14. $^1$H NMR (400 MHz, CDCl$_3$): δ 6.89-7.02 (m, 3H), 4.97 (s, 2H), 1.70 (q, J=7.6 Hz, 2H), 1.26 (s, 6H), 0.84 (t, J=7.6 Hz, 3H). LC-MS (m/z) 258.3 (M+H$^+$).

Compound 15: N-(4-chlorobenzyl)-N-hydroxy-2,2-dimethylbutanamide

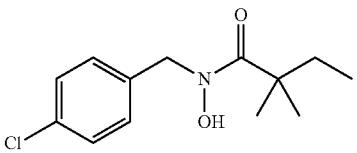 [SMILES: CCC(C)(C)C(=O)N(O)Cc1ccc(Cl)cc1]

The titled compound 15 was prepared in 40% yield from 4-chlorobenzaldehyde (300 mg), hydroxylamine hydrochloride (163 mg), 8M pyridine-borane complex (0.53 mL) and 2,2-dimethylbutanoylchloride (314 mg) according to the procedure outlined for compound 9. $^1$H NMR (400 MHz, CDCl$_3$) δ (ppm): 7.31-7.34 (m, 2H), 7.18-7.25 (m, 2H), 4.85 (s, 2H), 1.68 (q, J=7.6 Hz, 2H), 1.25 (s, 6H), 0.84 (t, J=7.6 Hz, 3H). LC-MS (m/z) 256.3 (M+H$^+$).

Compound 16: N-(4-chloro-3-fluorobenzyl)-N-hydroxy-2,2-dimethylbutanamide

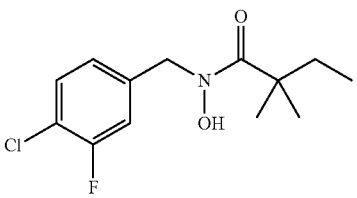 [SMILES: CCC(C)(C)C(=O)N(O)Cc1ccc(Cl)c(F)c1]

The titled compound 16 was prepared in 61.4% yield from N-(4-chloro-3-fluorobenzyl)hydroxylamine (300 mg) and 2,2-dimethylbutanoylchloride (252 mg) according to the procedure outlined for compound 9. $^1$H NMR (400 MHz, CDCl$_3$) δ (ppm): 7.38 (t, J=8.0 Hz, 1H), 7.12 (dd, J=2.0 Hz, 9.6 Hz, 1H) 7.03-7.06 (m, 1H), 4.85 (s, 2H), 1.68 (q, J=7.6 Hz, 2H), 1.26 (s, 6H), 0.86 (t, J=7.6 Hz, 3H). LC-MS (m/z) 274.7 (M+H$^+$).

Compound 17: N-(3-chloro-5-fluorobenzyl)-N-hydroxy-2,2-dimethylbutanamide

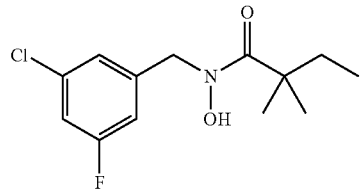 [SMILES: CCC(C)(C)C(=O)N(O)Cc1cc(F)cc(Cl)c1]

The titled compound 17 was prepared in 65% yield from N-(3-chloro-5-fluorobenzyl)hydroxylamine (300 mg) and 2,2-dimethylbutanoylchloride (252 mg) according to the procedure outlined for compound 9. $^1$H NMR (400 MHz, CDCl$_3$) δ (ppm): 7.10 (s, 1H), 7.04 (dt, 1H, J=2.0 Hz, 8.4 Hz), 6.93-6.96 (m, 1H), 4.85 (s, 2H), 1.68 (q, J=7.2 Hz, 2H), 1.27 (s, 6H), 0.87 (t, J=7.2 Hz, 3H). LC-MS (m/z) 274.4 (M+H$^+$).

Compound 18: N-(4-bromobenzyl)-N-hydroxy-2,2-dimethylbutanamide

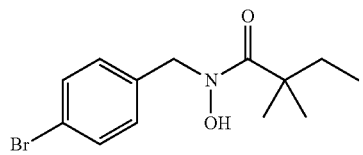

The titled compound 18 was prepared in 40% yield from 4-bromobenzaldehyde (400 mg), hydroxylamine hydrochloride (165 mg), 8M pyridine-borane complex (0.56 mL) and 2,2-dimethylbutanoylchloride (358 mg) according to the procedure outlined for compound 9. 1H NMR (400 MHz, CDCl$_3$) δ 7.47 (d, J=8.4 Hz, 2H), 7.17 (d, J=8.5 Hz, 2H), 4.82 (s, 2H), 1.66 (q, J=7.5 Hz, 2H), 1.24 (s, 6H), 0.83 (t, J=7.5 Hz, 3H). LC-MS (m/z) 300.2, 302.3 (M+H$^+$).

Compound 19: N-benzyl-N-hydroxy-2,2-dimethylbut-3-enamide

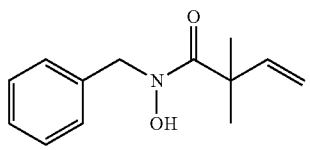 [SMILES: C=CC(C)(C)C(=O)N(O)Cc1ccccc1]

A mixture of n-benzylhydroxylamine hydrochloride (140 mg), 2,2-dimethylbut-3-enoic acid (100 mg) and N-(3-Dimethylaminopropyl)-N'-ethylcarbodiimide hydrochloride (252 mg) were dissolved in dry DMF (5 mL), and 0.45 mL of DIEA was added. The reaction mixtures were stirred at room temperature for overnight. The mixture was extracted with EtOAc, washed with water and brine, dried (Na$_2$SO4), and concentrated in vacuo. Purification by pre-HPLC to give compound 19 (14 mg, 7.3%)

$^1$H NMR (400 MHz, CDCl$_3$) δ 7.39-7.24 (m, 4H), 6.03 (dd, J=17.7, 10.5 Hz, 1H), 5.08 (dt, J=13.5, 2.5 Hz, 2H), 4.85 (s, 2H), 1.36 (d, J=1.3 Hz, 6H). LC-MS (m/z) 220.4 (M+H$^+$).

Compound 20: N-((2,3-dihydro-1H-inden-5-yl)methyl)-N-hydroxy-2,2-dimethylbutanamide

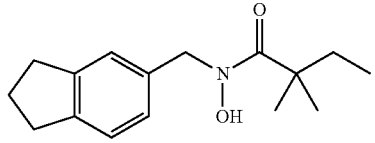 [SMILES: CCC(C)(C)C(=O)N(O)Cc1ccc2c(c1)CCC2]

The titled compound 20 was prepared in 40% yield from 2,3-dihydro-1H-indene-5-carbaldehyde (250 mg), hydroxylamine hydrochloride (130 mg), 8M pyridine-borane complex (0.35 mL) and 2,2-dimethylbutanoylchloride (544 mg) according to the procedure outlined for compound 9. $^1$H NMR (400 MHz, CDCl3) δ (ppm): 7.21 (d, J=7.6 Hz, 1H), 7.17 (s, 1H), 7.07 (d, 1H, J=7.6 Hz), 4.87 (s, 2H), 2.89 (t, J=7.2 Hz, 4H), 2.04-2.11 (m, 2H), 1.69 (q, J=7.6 Hz, 2H), 1.27 (s, 6H), 0.88 (t, J=7.6 Hz, 3H). LC-MS (m/z) 262.4 (M+H$^+$).

Compound 21: N-((4,5-dimethylthiophen-2-yl)methyl)-N-hydroxy-2,2-dimethylbutanamide

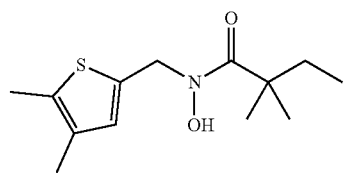 [SMILES: CCC(C)(C)C(=O)N(O)Cc1cc(C)c(C)s1]

The titled compound 21 was prepared in 86% yield from N-((4,5-dimethylthiophen-2-yl)methyl)hydroxylamine (200 mg) and 2,2-dimethylbutanoylchloride (189 mg) according to the procedure outlined for compound 9. $^1$H NMR (400 MHz, CDCl3) δ (ppm): 6.72 (s, 1H), 4.90 (s, 2H), 2.30 (s, 3H), 2.08 (s, 3H), 1.69 (q, J=7.6 Hz, 2H), 1.26 (s, 6H), 0.85 (t, J=7.6 Hz, 3H). LC-MS (m/z) 256.14 (M+H$^+$).

Compound 22: N-hydroxy-2,2-dimethyl-N-((3-methylthiophen-2-yl)methyl)butanamide

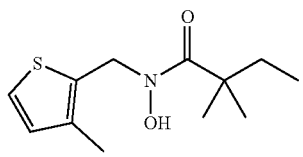 [SMILES: CCC(C)(C)C(=O)N(O)Cc1sccc1C]

The titled compound 22 was prepared in 15% yield from N-((3-methylthiophen-2-yl)methyl)hydroxylamine (200 mg) and 2,2-dimethylbutanoylchloride (284 mg) according to the procedure outlined for compound 9. $^1$H NMR (300 MHz, DMSO-d6) 9.76 (bs, 1H), 7.28 (d, J=8.2 MHz, 1H), 6.81 (d, J=5.76 Hz, 1H), 4.56 (bs, 2H), 1.68 (q, J=7.2 Hz, 2H), 1.25 (s, 6H), 0.83 (t, J=7.2 Hz, 3H). LC-MS (m/z) 242.4 (M+H$^+$).

Compound 23: N-hydroxy-2,2-dimethyl-N-(thiophen-3-ylmethyl)butanamide

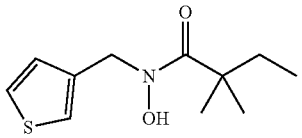

The titled compound 23 was prepared in 15% yield from N-(thiophen-3-ylmethyl)hydroxylamine (200 mg) and 2,2-dimethylbutanoylchloride (289 mg) according to the procedure outlined for compound 9. $^1$H NMR (400 MHz, CDCl$_3$) δ (ppm): 7.32 (dd, J=3.2 Hz, 5.2 Hz, 1H), 7.23-7.24 (m, 1H), 7.07 (dd, J=1.2 Hz, 4.8 Hz, 1H), 4.88 (s, 2H), 1.68 (q, J=7.2 Hz, 2H), 1.25 (s, 6H), 0.83 (t, J=7.2 Hz, 3H). LC-MS (m/z) 228.3 (M+H$^+$).

Compound 24: N-hydroxy-2,2-dimethyl-N-((2-methylthiazol-5-yl)methyl)butanamide

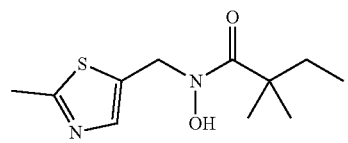 [SMILES: CCC(C)(C)C(=O)N(O)Cc1cnc(C)s1]

The titled compound 24 was prepared in 29% yield from tert-butyl (tert-butoxycarbonyl)oxycarbamate (185 mg), 5-(bromomethyl)-2-methylthiazole (140 mg) and 2,2-dimethylbutanoylchloride (130 mg) according to the procedure outlined for compound 9. $^1$H NMR (400 MHz, CDCl$_3$) δ (ppm): 7.36 (s, 1H), 4.88 (s, 2H), 2.63 (s, 3H), 1.74 (q, J=7.2 Hz, 2H), 1.27 (s, 6H), 0.84 (t, J=7.2 Hz, 3H). LC-MS (m/z) 243.3 (M+H$^+$).

Compound 25: N-(cyclohex-1-en-1-ylmethyl)-N-hydroxy-2,2-dimethylbutanamide

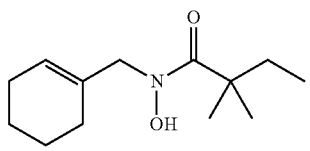 [SMILES: CCC(C)(C)C(=O)N(O)CC1=CCCCC1]

The titled compound 25 was prepared in 28% yield from tert-butyl (tert-butoxycarbonyl)oxycarbamate (275 mg), 1-(bromomethyl)cyclohex-1-ene (187 mg) and 2,2-dimethylbutanoylchloride (175 mg) according to the procedure outlined for compound 9. $^1$H NMR (400 MHz, CDCl$_3$) δ (ppm): 5.63-5.66 (m, 1H), 4.21 (s, 2H), 2.03-2.07 (m, 2H), 1.91-1.95 (m, 2H), 1.67 (q, J=7.6 Hz, 2H), 1.63-1.66 (m, 2H), 1.56-1.62 (m, 2H), 1.25 (s, 6H), 0.87 (t, J=7.6 Hz, 3H). LC-MS (m/z) 226.3 (M+H$^+$).

Compound 26: N-(3,5-difluorobenzyl)-N-hydroxy-2,2-dimethylbutanamide-3,4-d2

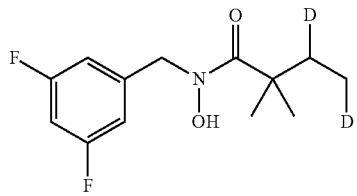 [SMILES: [2H]CC([2H])C(C)(C)C(=O)N(O)Cc1cc(F)cc(F)c1]

2,2-dimethylbut-3-enoic acid (5.0 g) and platinum oxide (250 mg) in methan(2H)ol (25 mL) was stirred at room temperature under $D_2$ for 3 hours. The catalyst was filtered off and washed with methan(2H)ol. The filtrate was concentrated in vacuo to give 2,2-dimethylbut-3-enoic acid-3,4-d2 (5.0 g) $^1$H NMR (400 MHz, DMSO) δ 12.00 (s, 1H), 1.40-1.46 (m, 1H), 1.04 (s, 6H), 0.80-0.70 (m, 2H).

Under argon, oxalyl chloride (8.06 g, 63.5 mmol, 1.5 equiv) was added to a solution of 2,2-dimethylbut-3-enoic acid-3,4-d2 (5.0 g, 42.3 mmol, 1 equiv) in dichloromethane (100 mL) over a period of 20 minute at 0° C. The reaction mixture was stirred at 20° C. for 2 h, then concentrated in vacuo to give an intermediate acid chloride, as a light yellow free-flowing liquid. A solution of N-(3,5-difluorobenzyl) hydroxylamine (6.12 g, 38.5 mmol) and Et₃N (10.6 mL) in dry DCM (87 mL) was cooled to 0° C., and the above acid chloride in dry DCM (5 mL) was added. The mixtures were stirred at for 1 h and room temperature for overnight. The mixture were extracted with EtOAc and the combined organic layer washed with brine, dried (Na₂SO4) and concentrated in vacuo. Purification by silica gel chromatography (EA/PE=1/5) to give compound 26 (4.4 g, 44%) as a white solid.

$^1$H NMR (400 MHz, DMSO) δ 9.77 (s, 1H), 7.10 (tt, J=9.4, 2.4 Hz, 1H), 6.94-6.88 (m, 2H), 4.66 (s, 2H), 1.65-1.57 (m, 1H), 1.13 (s, 6H), 0.74-0.68 (m, 2H). LC-MS (m/z) 260.3 (M+H⁺).

Compound 27: N-benzyl-N-hydroxy-2,2-dimethylbutanamide-3,4-d2

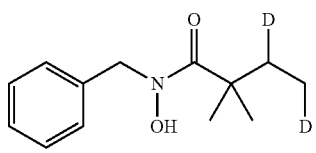 [SMILES: [2H]CC([2H])C(C)(C)C(=O)N(O)Cc1ccccc1]

The titled compound 27 was prepared in 43% yield from n-benzylhydroxylamine hydrochloride (250 mg) and 2,2-dimethylbutanoyl-3,4-d2 chloride (258.5 mg) according to the procedure outlined for compound 26. $^1$H NMR (400 MHz, DMSO) δ 9.55 (s, 1H), 7.32-7.26 (m, 2H), 7.25-7.19 (m, 3H), 4.64 (s, 2H), 1.60 (dt, J=14.0, 7.2 Hz, 1H), 1.12 (s, 6H), 0.71 (q, J=7.2 Hz, 2H). LC-MS (m/z) 224.3 (M+H⁺).

Compound 28: N-benzyl-N-hydroxy-2,2-dimethylbutanamide-3,3,4,4-d4

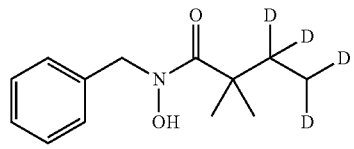 [SMILES: [2H]C([2H])C([2H])([2H])C(C)(C)C(=O)N(O)Cc1ccccc1]

2,2-dimethylbut-3-ynoic acid (200 mg) and palladium hydroxide (10 mg) in methan(2H)ol (2 mL) was stirred at room temperature under $D_2$ for 3 hours. The catalyst was filtered off and washed with methan(2H)ol. The filtrate was concentrated in vacuo to give 2,2-dimethylbutanoic-3,3,4,4-d4 acid (156 mg, 75%), $^1$H NMR (400 MHz, CDCl₃) δ 1.22-1.17 (m, 6H), 0.90-0.84 (m, 1H).

Under argon, oxalyl chloride (0.17 mL) was added to a solution of 2,2-dimethylbutanoic-3,3,4,4-d4 acid (156 mg) in dichloromethane (2 mL) over a period of 2 minute at 0° C. The reaction mixture was stirred at 20° C. for 2 h, then concentrated in vacuo to give an intermediate acid chloride, as a light yellow free-flowing liquid, which was directly used for next step without purification.

A solution of n-benzylhydroxylamine hydrochloride (207 mg) in dry DCM (5 mL) was cooled to 0° C., and the above acid chloride in dry DCM (2 mL) was added. The mixtures were stirred at for 1 h and room temperature for overnight. The mixture were extracted with EtOAc and the combined organic layer washed with brine, dried (Na₂SO4) and concentrated in vacuo. Purification by silica gel chromatography (EA/PE=1/5) to give compound 28 (99 mg, 34%) as white solid. $^1$H NMR (400 MHz, CDCl₃) δ 7.42-7.27 (m, 5H), 4.90 (s, 2H), 1.25 (s, 6H), 0.85-0.78 (m, 1H). LC-MS (m/z) 226.3 (M+H⁺).

Compound 29: N-(4-fluorobenzyl)-N-hydroxy-2,2-dimethylbutanamide-3,3,4,4-d4

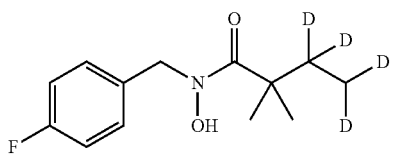 [SMILES: [2H]C([2H])C([2H])([2H])C(C)(C)C(=O)N(O)Cc1ccc(F)cc1]

The titled compound 29 was prepared in 30.1% yield from N-(4-fluorobenzyl)hydroxylamine (235 mg), 2,2-dimethylbutanoic-3,3,4,4-d4 acid (220 mg) and oxalyl chloride (349 mg) according to the procedure outlined for compound 28. $^1$H NMR (400 MHz, CDCl₃) δ (ppm): 7.27-7.31 (m, 2H), 7.02-7.07 (m, 2H), 4.86 (s, 2H), 1.25 (s, 6H), 0.79-0.83 (m, 1H). LC-MS (m/z) 244.4 (M+H⁺).

Compound 30: N-hydroxy-2,2-dimethyl-N-((phenyl-d5)methyl-d2)butanamide

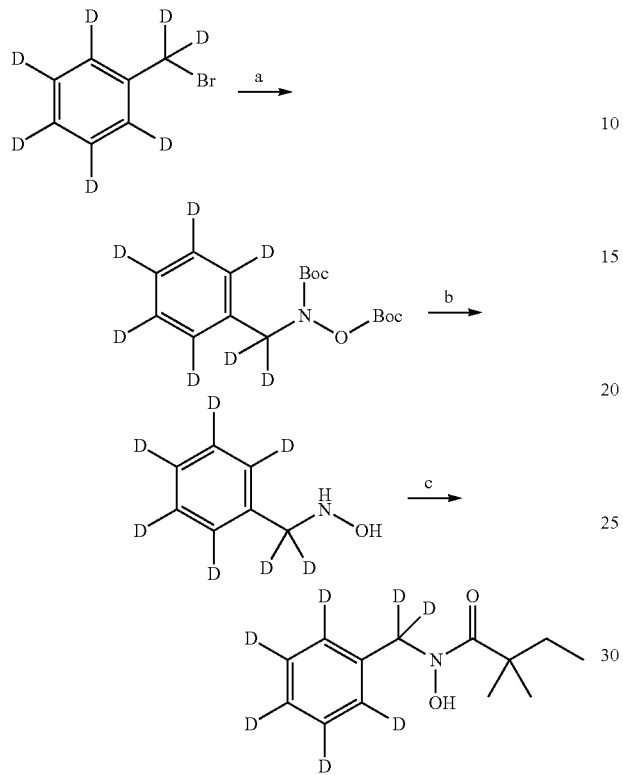

Reagent and conditions: (a) tert-butyl (tert-butoxycarbonyl)oxycarbamate, 1N NaOH, TBAB, DCM; (b) TFA, DCM; (c) 2,2-dimethylbutanoyl chloride, aq. NaHCO₃, THF, H₂O. Tert-butyl (tert-butoxycarbonyl)oxycarbamate (400 mg) and 1-(bromomethyl-d2)benzene-2,3,4,5,6-d5 (100 mg) were dissolved in CH$_2$Cl$_2$ (4 ml). The mixture was added 1M NaOH (2 ml) and tetrabutylammonium bromide (25.2 mg), and stirred at room temperature for overnight. The resulting mixture was washed with water and dried with Na$_2$SO$_4$, concentrated in vacuo and purification by silica gel chromatography to give tert-butyl ((tert-butoxycarbonyl)oxy)((phenyl-d5)methyl-d2)carbamate (510 mg, 99%). $^1$HNMR (400 MHz, CDCl$_3$) δ 1.46 (s, 9H), 1.44 (s, 9H).

The above intermediate was dissolved in CH$_2$Cl$_2$ (10 ml), TFA (3 ml) was added at 0° C. The mixture was stirred at room temperature for 4 h and concentrated to give N-(2,3,5-trifluorobenzyl)hydroxylamine (354 mg) as a TFA salt, which was used for next step without further purification.

The above intermediate was dissolved in THF (2.5 ml) and water (2.5 ml) and 1 ml of saturated aqueous NaHCO$_3$ was added. The mixture was stirred at room temperature for 30 min, then cooled to 0° C., 2,2-dimethylbutanoylchloride (0.24 mL) was added and stirred for overnight. The mixture was extracted with EtOAc, washed with brine, dried (Na$_2$SO4), and concentrated in vacuo. Purification by silica gel chromatography to give compound 30 (124 mg, total yield 35%). $^1$H NMR (400 MHz, CDCl$_3$) δ 1.67 (q, J=7.5 Hz, 2H), 1.25 (s, 6H), 0.85 (t, J=7.5 Hz, 3H). LC-MS (m/z) 229.4 (M+H⁺).

Compound 31: N-hydroxy-2,2-dimethyl-N-((phenyl-d5)methyl-d2)butanamide-3,4-d2

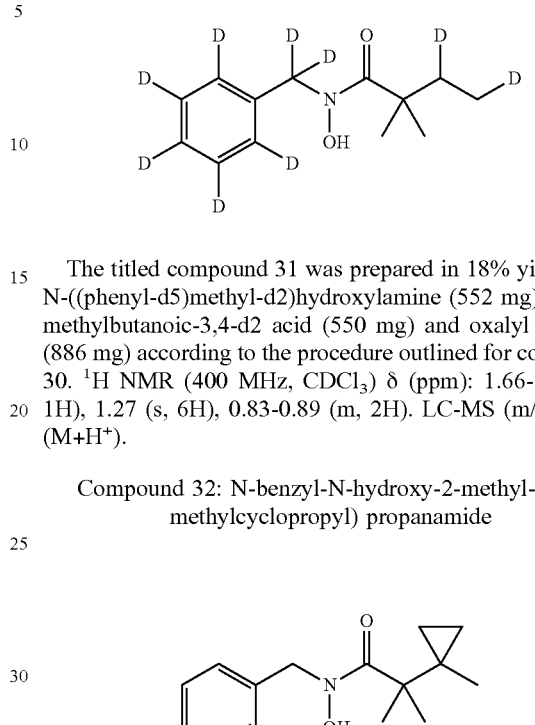

The titled compound 31 was prepared in 18% yield from N-((phenyl-d5)methyl-d2)hydroxylamine (552 mg), 2,2-dimethylbutanoic-3,4-d2 acid (550 mg) and oxalyl chloride (886 mg) according to the procedure outlined for compound 30. $^1$H NMR (400 MHz, CDCl$_3$) δ (ppm): 1.66-1.69 (m, 1H), 1.27 (s, 6H), 0.83-0.89 (m, 2H). LC-MS (m/z) 231.4 (M+H⁺).

Compound 32: N-benzyl-N-hydroxy-2-methyl-2-(1-methylcyclopropyl) propanamide

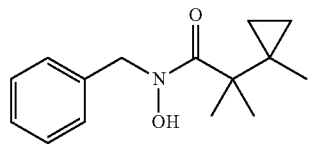 [SMILES: CC1(C(C)(C)C(=O)N(O)Cc2ccccc2)CC1]

Under argon, oxalyl chloride (102.3 mg, 0.732 mmol, 2.2 equiv) was added to a solution of 2-methyl-2-(1-methylcyclopropyl)propanoic acid (52 mg, 0.366 mmol, 1 equiv) in dichloromethane (2 mL) over a period of 2 minute at 0° C. The reaction mixture was stirred at room temperature for 2 h, then concentrated in vacuo to give an intermediate acid chloride, as a light yellow free-flowing liquid. A solution of n-benzylhydroxylamine hydrochloride (58.4 mg, 0.366 mmol) was dissolved in 1 ml of THF/H$_2$O (1:1, v/v) and 0.22 ml of saturated aqueous NaHCO$_3$. The solution was cooled to 0° C. and 2-methyl-2-(1-methylcyclopropyl)propanoyl chloride (59 mg) was added and the mixture was stirred at room temperature for 16 h. The mixture was extracted with EtOAc and the combined organic layer washed with brine, dried (Na$_2$SO$_4$) and concentrated in vacuo. Purification by silica gel chromatography to give compound 32 (136 mg, 40%) s white solid. $^1$H NMR (400 MHz, CDCl$_3$) δ 7.42-7.24 (m, 5H), 5.04 (s, 2H), 1.14 (s, 6H), 1.03 (s, 3H), 0.71-0.66 (m, 2H), 0.39 (q, J=4.8 Hz, 2H). LC-MS (m/z) 248.4 (M+H⁺).

Compound 33: N-benzyl-N-hydroxycyclopentanecarboxamide

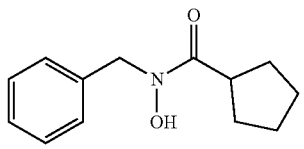 [SMILES: O=C(C1CCCC1)N(O)Cc1ccccc1]

n-benzylhydroxylamine hydrochloride (100 mg) was dissolved in 2 ml of THF/H$_2$O (1:1) and 0.4 ml of saturated aqueous NaHCO$_3$. The solution was cooled to 0° C. and cyclopentanecarbonyl chloride (91.5 mg) was added and the mixture was stirred at room temperature for 16 h. The mixture was extracted with EtOAc and the combined organic layer washed with brine, dried (Na$_2$SO4) and concentrated in vacuo. Purification by silica gel chromatography to give compound 33. (59 mg, 43%).

$^1$H NMR (400 MHz, CDCl$_3$) δ (ppm): 7.33-7.39 (m, 2H), 7.28-7.32 (m, 3H), 4.88 (s, 2H), 2.84-2.90 (m, 1H), 1.74-1.92 (m, 6H), 1.54-1.63 (m, 2H). LC-MS (m/z) 220.3 (M+H$^+$).

Compound 34: N-benzyl-N-hydroxy-1-(trifluoromethyl)cyclopentane-1-carboxamide

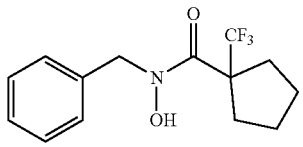 [SMILES: O=C(N(O)Cc1ccccc1)C1(C(F)(F)F)CCCC1]

The titled compound 34 was prepared in 28% yield from n-benzylhydroxylamine hydrochloride (72 mg), 1-(trifluoromethyl)cyclopentane-1-carboxylic acid (100 mg), and oxalyl chloride (104 mg) according to the procedure outlined for compound 32. $^1$H NMR (400 MHz, CDCl$_3$) δ (ppm): 7.31-7.40 (m, 3H), 7.27-7.30 (m, 2H), 4.92 (s, 2H), 2.43-2.50 (m, 2H), 2.14-2.21 (m, 2H), 1.64-1.75 (m, 4H). LC-MS (m/z) 288.3 (M+H$^+$)

Compound 35: N-benzyl-N-hydroxy-1-(trifluoromethyl)cyclobutane-1-carboxamide

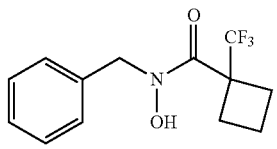 [SMILES: O=C(N(O)Cc1ccccc1)C1(C(F)(F)F)CCC1]

The titled compound 35 was prepared in 30% yield from n-benzylhydroxylamine hydrochloride (48 mg), 1-(trifluoromethyl)cyclobutane-1-carboxylic acid (50 mg), and oxalyl chloride (113 mg) according to the procedure outlined for compound 32. $^1$H NMR (400 MHz, CDCl$_3$) δ 7.40-7.29 (m, 3H), 7.30-7.25 (m, 2H), 4.82 (s, 2H), 2.73 (dd, J=22.8, 10.0 Hz, 2H), 2.50 (t, J=10.2 Hz, 2H), 2.16-2.02 (m, 1H), 1.91-1.78 (m, 1H). LC-MS (m/z) 274.3 (M+H$^+$).

Compound 36: N-benzyl-N-hydroxy-1-methylcyclohexane-1-carboxamide

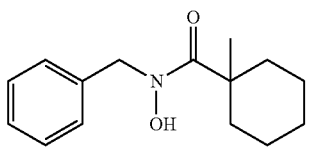 [SMILES: CC1(C(=O)N(O)Cc2ccccc2)CCCCC1]

The titled compound 36 was prepared in 19.2% yield from n-benzylhydroxylamine hydrochloride (100 mg), 1-methylcyclohexane-1-carboxylic acid (100 mg), and oxalyl chloride (134 mg) according to the procedure outlined for compound 32. $^1$H NMR (400 MHz, CDCl$_3$) δ (ppm): 7.35-7.39 (m, 2H), 7.29-7.32 (m, 3H), 4.94 (s, 2H), 2.10-2.15 (m, 2H), 1.46-1.57 (m, 5H), 1.33-1.41 (m, 3H), 1.25 (s, 3H). LC-MS (m/z) 248.3 (M+H$^+$).

Compound 37: N-benzyl-N-hydroxycyclohexanecarboxamide

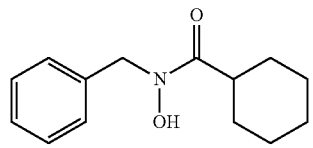 [SMILES: O=C(C1CCCCC1)N(O)Cc1ccccc1]

The titled compound 37 was prepared in 30.2% yield from n-benzylhydroxylamine hydrochloride (229 mg), cyclohexanecarboxylic acid (300 mg), and oxalyl chloride (519.46 mg) according to the procedure outlined for compound 32. $^1$H NMR (400 MHz, CDCl$_3$) δ 7.41-7.25 (m, 5H), 4.84 (s, 2H), 2.52-2.36 (m, 1H), 1.87-1.41 (m, 7H), 1.36-1.12 (m, 3H). LC-MS (m/z) 243.3 (M+H$^+$).

Compound 38: N-benzyl-1-ethyl-N-hydroxycyclopropane-1-carboxamide

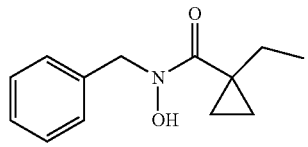 [SMILES: CCC1(C(=O)N(O)Cc2ccccc2)CC1]

The titled compound 38 was prepared in 53% yield from n-benzylhydroxylamine hydrochloride (254 mg), 1-ethylcyclopropane-1-carboxylic acid (200 mg), and oxalyl chloride (334 mg) according to the procedure outlined for compound 32. $^1$H NMR (400 MHz, CDCl$_3$) δ (ppm): 8.15 (brs, 1H), 7.36-7.40 (m, 2H), 7.28-7.33 (m, 3H), 5.01 (s, 2H), 1.55 (q, J=7.2 Hz, 2H), 1.01 (t, J=7.2 Hz, 3H), 0.98-0.99 (m, 2H), 0.65-0.68 (m, 2H). LC-MS (m/z) 220.4 (M+H$^+$).

Compound 39: 1-ethyl-N-(4-fluorobenzyl)-N-hydroxycyclopropane-1-carboxamide

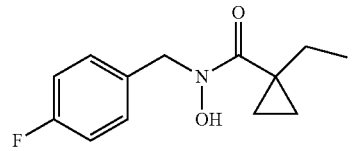 [SMILES: CCC1(C(=O)N(O)Cc2ccc(F)cc2)CC1]

The titled compound 39 was prepared in 27% yield from N-(4-fluorobenzyl)hydroxylamine (230 mg) and 1-ethylcyclopropane-1-carbonyl chloride (222 mg) according to the procedure outlined for compound 32. $^1$HNMR (400 MHz, CDCl$_3$) δ (ppm): 7.26-7.29 (m, 2H), 7.04-7.09 (m, 2H), 4.97

(s, 2H), 1.54 (q, J=7.2 Hz, 2H), 1.00 (t, J=7.2 Hz, 3H), 0.97-0.98 (m, 2H), 0.66-0.69 (m, 2H). LC-MS (m/z) 238.3 (M+H⁺).

Compound 40: N-(4-chlorobenzyl)-1-ethyl-N-hydroxycyclopropane-1-carboxamide

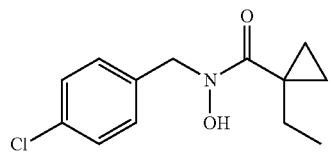 [SMILES: CCC1(C(=O)N(O)Cc2ccc(Cl)cc2)CC1]

The titled compound 40 was prepared in 20% yield from N-(4-chlorobenzyl)hydroxylamine (247 mg) and 1-ethylcyclopropane-1-carbonyl chloride (230 mg) according to the procedure outlined for compound 32. 1H NMR (400 MHz, CDCl₃) δ (ppm): 7.33-7.37 (m, 2H), 7.22-7.24 (m, 2H), 4.97 (s, 2H), 1.53 (q, J=7.6 Hz, 2H), 1.00 (t, J=7.6 Hz, 3H), 0.96-0.99 (m, 2H), 0.66-0.68 (m, 2H). LC-MS (m/z) 254.7 (M+H⁺).

Compound 41: N-(3,5-difluorobenzyl)-1-ethyl-N-hydroxycyclopropane-1-carboxamide

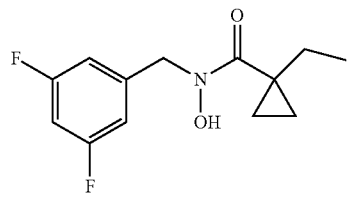 [SMILES: CCC1(C(=O)N(O)Cc2cc(F)cc(F)c2)CC1]

The titled compound 41 was prepared in 7.5% yield from N-(3,5-difluorobenzyl)hydroxylamine (247 mg) and 1-ethylcyclopropane-1-carbonyl chloride (230 mg) according to the procedure outlined for compound 32. ¹H NMR (400 MHz, CDCl₃) δ (ppm): 6.81-6.86 (m, 2H), 6.73-6.79 (m, 1H), 4.97 (s, 2H), 1.52 (q, J=7.2 Hz, 2H), 1.00 (t, J=7.6 Hz, 3H), 0.96-0.98 (m, 2H), 0.66-0.69 (m, 2H). LC-MS (m/z) 256.3 (M+H⁺).

Compound 42: N-(4-bromobenzyl)-3,3,3-trifluoro-N-hydroxy-2,2-dimethylpropanamide

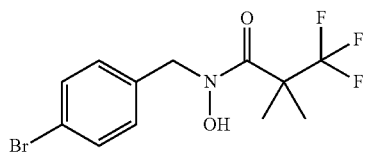

The titled compound 42 was prepared in 7.5% yield from N-(4-bromobenzyl)hydroxylamine (247 mg) and 3,3,3-trifluoro-2,2-dimethylpropanoyl chloride (230 mg) according to the procedure outlined for compound 32. ¹H NMR (400 MHz, CDCl₃) δ (ppm): 7.48-7.52 (m, 2H), 7.17-7.20 (m, 2H), 4.83 (s, 2H), 1.54 (s, 6H). LC-MS (m/z) 240.1, 242.2 (M+H⁺).

Compound 43: 3,3,3-trifluoro-N-(4-fluorobenzyl)-N-hydroxy-2,2-dimethylpropanamide

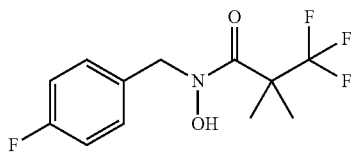 [SMILES: CC(C)(C(=O)N(O)Cc1ccc(F)cc1)C(F)(F)F]

The titled compound 43 was prepared in 27% yield from N-(4-fluorobenzyl)hydroxylamine (162 mg) and 3,3,3-trifluoro-2,2-dimethylpropanoyl chloride (223 mg) according to the procedure outlined for compound 32. ¹H NMR (400 MHz, CDCl₃) δ (ppm): 7.27-7.29 (m, 2H), 7.03-7.07 (m, 2H), 4.83 (s, 2H), 1.54 (s, 6H). LC-MS (m/z) 280.3 (M+H⁺).

Compound 44: N-(4-chlorobenzyl)-3,3,3-trifluoro-N-hydroxy-2,2-dimethylpropanamide

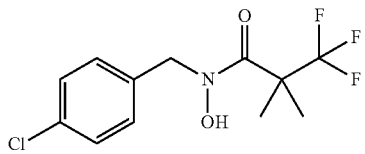 [SMILES: CC(C)(C(=O)N(O)Cc1ccc(Cl)cc1)C(F)(F)F]

The titled compound 44 was prepared in 33% yield from N-(4-chlorobenzyl)hydroxylamine (271 mg) and 3,3,3-trifluoro-2,2-dimethylpropanoyl chloride (330 mg) according to the procedure outlined for compound 32. ¹H NMR (400 MHz, CDCl₃) δ (ppm): 7.33-7.36 (m, 2H), 7.23-7.25 (m, 2H), 4.86 (s, 2H), 1.54 (s, 6H). LC-MS (m/z) 296.7 (M+H⁺).

Compound 45: N-(3,5-difluorobenzyl)-3,3,3-trifluoro-N-hydroxy-2,2-dimethylpropanamide

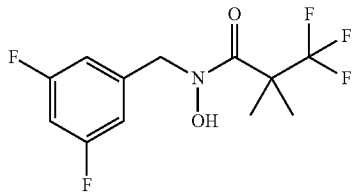 [SMILES: CC(C)(C(=O)N(O)Cc1cc(F)cc(F)c1)C(F)(F)F]

The titled compound 45 was prepared in 34% yield from N-(3,5-difluorobenzyl)hydroxylamine (183 mg) and 3,3,3-trifluoro-2,2-dimethylpropanoyl chloride (223 mg) according to the procedure outlined for compound 32. ¹H NMR (400 MHz, CDCl₃) δ (ppm): 6.82-6.84 (m, 2H), 6.74-6.80 (m, 1H), 4.85 (s, 2H), 1.55 (s, 6H). LC-MS (m/z) 298.3 (M+H⁺).

Compound 46: 3,3,3-trifluoro-N-hydroxy-2,2-dimethyl-N-(3,4,5-trifluorobenzyl)propenamide

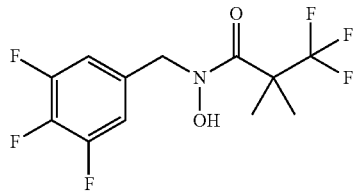 [SMILES: CC(C)(C(=O)N(O)Cc1cc(F)c(F)c(F)c1)C(F)(F)F]

The titled compound 46 was prepared in 34% yield from N-(3,4,5-trifluorobenzyl)hydroxylamine (305 mg) and 3,3,3-trifluoro-2,2-dimethylpropanoyl chloride (330 mg) according to the procedure outlined for compound 32. $^1$H NMR (400 MHz, CDCl$_3$) δ (ppm): 6.95 (t, 2H, J=6.8 Hz), 6.44 (brs, 1H), 4.79 (s, 2H), 1.54 (s, 6H). LC-MS (m/z) 316.3 (M+H$^+$).

Compound 47: N-((4,5-dimethylthiophen-2-yl)methyl)-3,3,3-trifluoro-N-hydroxy-2,2-dimethylpropanamide

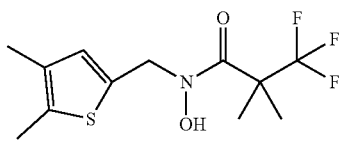 [SMILES: Cc1cc(CN(O)C(=O)C(C)(C)C(F)(F)F)sc1C]

The titled compound 47 was prepared in 14% yield from N-((4,5-dimethylthiophen-2-yl)methyl)hydroxylamine (200 mg) and 3,3,3-trifluoro-2,2-dimethylpropanoyl chloride (244 mg) according to the procedure outlined for compound 32. $^1$H NMR (400 MHz, CDCl$_3$) δ (ppm): 6.72 (s, 1H), 6.09 (bs, 1H), 4.89 (s, 2H), 2.31 (s, 3H), 2.09 (s, 3H), 1.54 (s, 6H). LC-MS (m/z) 276.3 (M+H$^+$).

Compound 48: 3,3,3-trifluoro-N-hydroxy-2,2-dimethyl-N-((3-methylthiophen-2-yl)methyl)propanamide

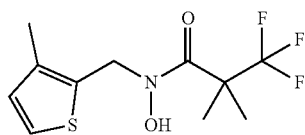 [SMILES: Cc1ccsc1CN(O)C(=O)C(C)(C)C(F)(F)F]

The titled compound 48 was prepared in 8.2% yield from N-((3-methylthiophen-2-yl)methyl)hydroxylamine (150 mg) and 3,3,3-trifluoro-2,2-dimethylpropanoyl chloride (168 mg) according to the procedure outlined for compound 32. $^1$H NMR (400 MHz, CDCl$_3$) δ (ppm): 7.20 (d, J=5.2 Hz, 1H), 6.85 (d, J=5.2 Hz, 1H), 4.97 (s, 2H), 2.24 (s, 3H), 1.54 (s, 6H). LC-MS (m/z) 282.3 (M+H$^+$).

Compound 49: 3,3,3-trifluoro-N-hydroxy-2,2-dimethyl-N-(thiophen-2-ylmethyl)propanamide

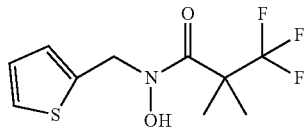 [SMILES: CC(C)(C(=O)N(O)Cc1cccs1)C(F)(F)F]

The titled compound 49 was prepared in 5% yield from N-(thiophen-2-ylmethyl)hydroxylamine (100 mg) and 3,3,3-trifluoro-2,2-dimethylpropanoyl chloride (170 mg) according to the procedure outlined for compound 32. $^1$H NMR (400 MHz, CDCl$_3$) δ (ppm): 7.28-7.30 (m, 1H), 7.05-7.06 (m, 1H), 6.98-7.00 (m, 1H), 5.01 (s, 2H), 1.53 (s, 6H). LC-MS (m/z) 268.3 (M+H$^+$).

Compound 50: N-benzyl-N-((ethoxycarbonyl)oxy)-2,2-dimethylbutanamide

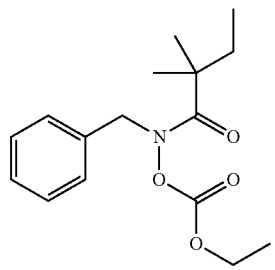 [SMILES: CCOC(=O)ON(Cc1ccccc1)C(=O)C(C)(C)CC]

To a cooled solution of N-benzyl-N-hydroxy-2,2-dimethylbutanamide (221 mg, 1 mmol) and DIEA (0.25 ml, 1.5 mmol) in 5 ml of dry DCM was added ethyl carbonochloridate (130.2 mg, 1.2 mmol). The mixture was stirred at room temperature for 2 h. The mixture were extracted with DCM and the combined organic layer washed with brine, dried (Na$_2$SO4) and concentrated in vacuo. Purification by silica gel chromatography (EA/PE=1/10) to give compound 50 (243 mg, 83%) as a colorless oil. 1H NMR (400 MHz, CDCl$_3$) δ 7.32-7.25 (m, 5H), 4.90 (s, 2H), 4.29 (q, J=7.1 Hz, 2H), 1.55 (q, J=7.5 Hz, 2H), 1.32 (t, J=7.1 Hz, 3H), 1.16 (s, 6H), 0.78 (t, J=7.5 Hz, 3H). LC-MS (m/z) 294.4 (M+H$^+$).

Compound 51: N-(benzoyloxy)-N-benzyl-2,2-dimethylbutanamide

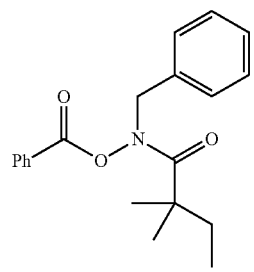 [SMILES: CCC(C)(C)C(=O)N(Cc1ccccc1)OC(=O)c1ccccc1]

The titled compound 51 was prepared in 65% yield from N-benzyl-N-hydroxy-2,2-dimethylbutanamide (221 mg, 1 mmol), benzoyl chloride (168 mg, 1.2 mmol), DIEA (0.25 ml, 1.5 mmol) according to the procedure outlined for compound 50.

$^1$H NMR (400 MHz, CDCl$_3$) δ 8.19-8.15 (m, 1H), 7.97-7.93 (m, 2H), 7.64 (ddd, J=7.1, 4.8, 1.2 Hz, 1H), 7.56-7.45 (m, 3H), 7.32-7.29 (m, 3H), 5.02 (s, 2H), 1.55 (q, J=7.5 Hz, 2H), 1.18 (s, 6H), 0.83 (t, J=7.5 Hz, 3H). LC-MS (m/z) 326.4 (M+H$^+$).

Compound 52: N,N'-(malonylbis(oxy))bis(N-benzyl-2,2-dimethylbutanamide)

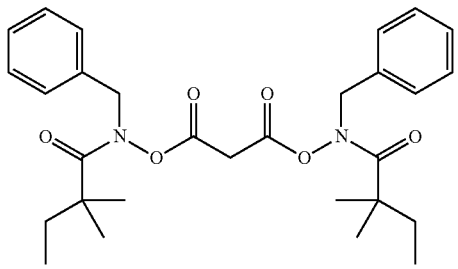 [SMILES: CCC(C)(C)C(=O)N(Cc1ccccc1)OC(=O)CC(=O)ON(Cc1ccccc1)C(=O)C(C)(C)CC]

To a cooled solution of N-benzyl-N-hydroxy-2,2-dimethylbutanamide (221 mg, 1 mmol) and pyridine (158.2 mg, 2 mmol) in 3 mL of dry DCM was added malonyl dichloride (140.95 mg, 0.5 mmol). The mixture was stirred at room temperature for 2 h. The mixture were extracted with DCM and the combined organic layer washed with brine, dried (Na$_2$SO4) and concentrated in vacuo. Purification by silica gel chromatography (EA/PE=1/10) to give compound (237.5 mg, 83%) as a colorless oil.

$^1$H NMR (400 MHz, CDCl$_3$) δ (ppm): 7.27-7.29 (m, 6H), 7.22-7.24 (m, 4H), 4.87 (s, 4H), 3.41 (s, 2H), 1.52 (q, J=7.6 Hz, 4H), 1.15 (s, 12H), 0.80 (t, J=7.6 Hz, 6H). LC-MS (m/z) 511.6 (M+H$^+$).

Compound 53: N,N'-(succinylbis(oxy))bis(N-benzyl-2,2-dimethylbutanamide)

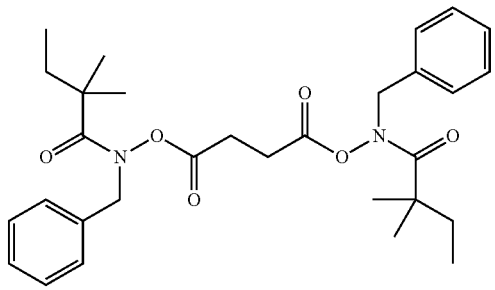 [SMILES: CCC(C)(C)C(=O)N(Cc1ccccc1)OC(=O)CCC(=O)ON(Cc1ccccc1)C(=O)C(C)(C)CC]

The titled compound 53 was prepared in 85% yield from N-benzyl-N-hydroxy-2,2-dimethylbutanamide (221 mg, 1 mmol), succinyl dichloride (72 mg, 0.5 mmol) and pyridine (158.2 mg, 2 mmol) according to the procedure outlined for compound 52.

$^1$H NMR (400 MHz, CDCl$_3$) δ 7.34-7.25 (m, 4H), 4.87 (s, 2H), 2.63 (s, 2H), 1.53 (q, J=7.5 Hz, 2H), 1.15 (s, 6H), 0.79 (t, J=7.5 Hz, 3H). LC-MS (m/z) 525.7 (M+H$^+$).

Compound 54: N,N'-(isophthaloylbis(oxy))bis(N-benzyl-2,2-dimethylbutanamide)

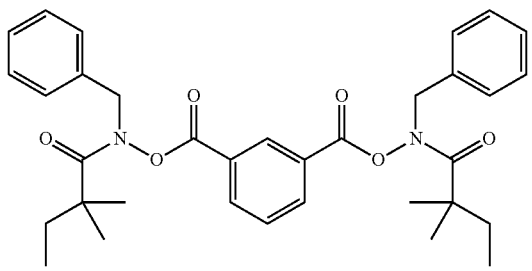 [SMILES: CCC(C)(C)C(=O)N(Cc1ccccc1)OC(=O)c1cccc(C(=O)ON(Cc2ccccc2)C(=O)C(C)(C)CC)c1]

The titled compound 54 was prepared in 78% yield from N-benzyl-N-hydroxy-2,2-dimethylbutanamide (221 mg, 1 mmol), isophthaloyl dichloride (101 mg, 0.5 mmol) and pyridine (158.2 mg, 2 mmol) according to the procedure outlined for compound 52.

$^1$H NMR (400 MHz, CDCl$_3$) δ 8.38 (t, J=1.6 Hz, 1H), 8.10 (dd, J=7.8, 1.6 Hz, 2H), 7.52 (t, J=7.8 Hz, 1H), 7.19-7.16 (m, 10H), 4.93 (s, 4H), 1.42 (q, J=7.5 Hz, 4H), 1.06 (s, 12H), 0.72 (t, J=7.5 Hz, 6H). LC-MS (m/z) 573.7 (M+H$^+$).

Compound 55: N,N'-(2,5,8,11-tetraoxadodecanedioylbis(oxy))bis(N-benzyl-2,2-dimethylbutanamide)

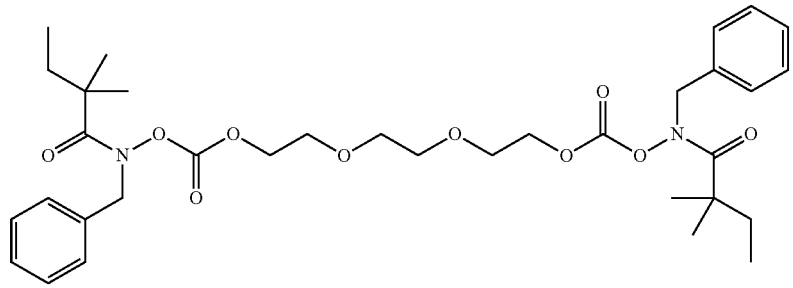 [SMILES: CCC(C)(C)C(=O)N(Cc1ccccc1)OC(=O)OCCOCCOCCOC(=O)ON(Cc1ccccc1)C(=O)C(C)(C)CC]

The titled compound 55 was prepared in 22% yield from N-benzyl-N-hydroxy-2,2-dimethylbutanamide (221 mg, 1 mmol), (ethane-1,2-diylbis(oxy))bis(ethane-2,1-diyl) bis(carbonochloridate) (137.5 mg, 0.5 mmol) and pyridine (0.12 mL, 1.5 mmol) according to the procedure outlined for compound 52. $^1$H NMR (400 MHz, CDCl$_3$) δ (ppm): 7.27-7.33 (m, 10H), 4.91 (s, 4H), 4.29-4.42 (m, 6H), 3.67-3.74 (m, 6H), 1.56 (q, J=7.6 Hz, 4H), 1.17 (s, 12H), 0.78 (t, J=7.6 Hz, 6H). LC-MS (m/z) 645.8 (M+H$^+$).

Compound 56: N-benzyl-2,2-dimethyl-N-((piperidine-1-carbonyl)oxy)butanamide

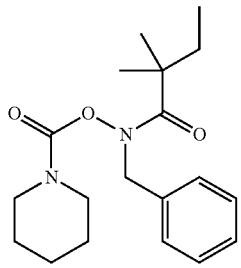 [SMILES: CCC(C)(C)C(=O)N(Cc1ccccc1)OC(=O)N1CCCCC1]

The titled compound 56 was prepared in 93% yield from N-benzyl-N-hydroxy-2,2-dimethylbutanamide (221 mg, 1 mmol), piperidine-1-carbonyl chloride (177.12 mg, 1.2 mmol), DIEA (0.33 ml, 2.0 mmol) according to the procedure outlined for compound 50. $^1$H NMR (400 MHz, CDCl$_3$) δ (ppm): 7.26-7.34 (m, 5H), 3.47 (s, 2H), 3.28 (s, 2H), 1.54-1.59 (m, 6H), 1.36-1.46 (m, 2H), 1.17 (s, 6H), 0.81 (t, J=7.6 Hz, 3H). LC-MS (m/z) 333.4 (M+H$^+$).

Compound 57: N-(([1,4'-bipiperidine]-1'-carbonyl)oxy)-N-benzyl-2,2-dimethylbutanamide

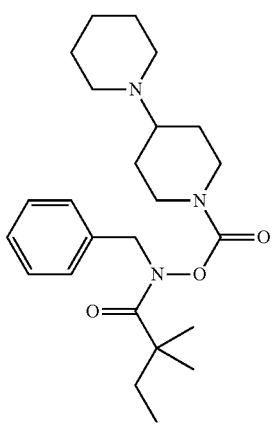 [SMILES: CCC(C)(C)C(=O)N(Cc1ccccc1)OC(=O)N1CCC(N2CCCCC2)CC1]

The titled compound 57 was prepared in 83% yield from N-benzyl-N-hydroxy-2,2-dimethylbutanamide (221 mg, 1 mmol), 1-chlorocarbonyl-4-piperidinopiperidine hydrochloride (320.64 mg, 1.2 mmol) and DIEA (0.6 ml) according to the procedure outlined for compound 50. $^1$H NMR (400 MHz, CDCl$_3$) δ (ppm): 7.27-7.32 (m, 3H), 7.23-7.25 (m, 2H), 4.25-4.40 (m, 1H), 3.85-4.00 (m, 1H), 3.58-3.69 (m, 2H), 3.16-3.21 (m, 1H), 2.91-3.03 (m, 2H), 2.80-2.86 (m, 2H), 2.25 (d, J=11.2 Hz, 2H), 1.96-2.17 (m, 4H), 1.57-1.68 (m, 3H), 1.50-1.54 (m, 5H), 1.14 (s, 6H), 0.81 (t, J=7.2 Hz, 3H). LC-MS (m/z) 416.6 (M+H$^+$).

Compound 58: N-benzyl-2,2-dimethyl-N-((phenoxycarbonyl)oxy)butanamide

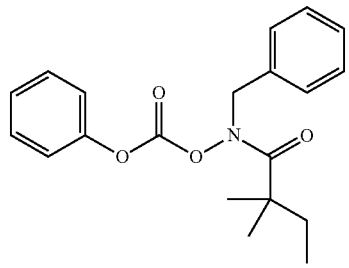 [SMILES: CCC(C)(C)C(=O)N(Cc1ccccc1)OC(=O)Oc1ccccc1]

The titled compound 58 was prepared in 54% yield from N-benzyl-N-hydroxy-2,2-dimethylbutanamide (330 mg, 1.49 mmol), phenyl carbonochloridate (349.4 mg, 1.79 mmol) and TEA (0.41 ml, 2.98 mmol) according to the procedure outlined for compound 50. 1H NMR (400 MHz, CDCl$_3$) δ 7.42-7.25 (m, 8H), 7.12 (d, J=1.2 Hz, 1H), 7.10 (d, J=1.0 Hz, 1H), 4.98 (s, 2H), 1.64 (q, J=7.5 Hz, 2H), 1.24 (s, 6H), 0.83 (t, J=7.5 Hz, 3H). LC-MS (m/z) 342.4 (M+H$^+$).

Compound 59: N-benzyl-N-((isobutoxycarbonyl)oxy)-2,2-dimethylbutanamide

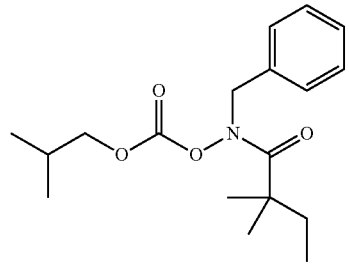 [SMILES: CCC(C)(C)C(=O)N(Cc1ccccc1)OC(=O)OCC(C)C]

The titled compound 59 was prepared in 96% yield from N-benzyl-N-hydroxy-2,2-dimethylbutanamide (330 mg, 1.49 mmol), isobutyl carbonochloridate (304 mg, 1.79 mmol) and TEA (0.41 ml, 2.98 mmol) according to the procedure outlined for compound 50. 1H NMR (400 MHz, CDCl$_3$) δ 7.33-7.25 (m, 5H), 4.90 (s, 2H), 4.02 (d, J=6.7 Hz, 2H), 1.98 (dp, J=13.4, 6.7 Hz, 1H), 1.55 (q, J=7.5 Hz, 2H), 1.16 (s, 6H), 0.94 (s, 3H), 0.92 (s, 3H), 0.77 (t, J=7.5 Hz, 3H). LC-MS (m/z) 322.4 (M+H$^+$).

Compound 60: N-benzyl-2,2-dimethyl-N-(nicotinoyloxy)butanamide

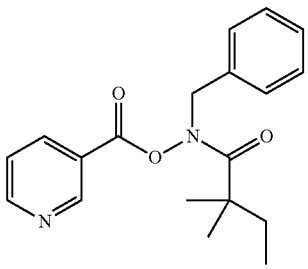 [SMILES: CCC(C)(C)C(=O)N(Cc1ccccc1)OC(=O)c1cccnc1]

The titled compound 60 was prepared in 56% yield from N-benzyl-N-hydroxy-2,2-dimethylbutanamide (221 mg, 1 mmol), pyridine-3-carbonyl chloride hydrochloride (178 mg, 1 mmol) and TEA (0.42 ml, 3 mmol) according to the procedure outlined for compound 50. $^1$H NMR (400 MHz, CDCl$_3$) δ (ppm): 9.11 (d, J=1.6 Hz, 1H), 8.86 (dd, J=1.6 Hz, 4.8 Hz, 1H), 8.23 (dt, J=2.0 Hz, 8.0 Hz, 1H), 7.47 (ddd, J=0.8 Hz, 5.2 Hz, 5.6 Hz, 1H), 7.28-7.31 (m, 5H), 5.04 (s, 2H), 1.56 (q, J=7.6 Hz, 2H), 1.19 (s, 6H), 0.84 (t, J=7.6 Hz, 3H). LC-MS (m/z) 327.4 (M+H$^+$).

Compound 61: N-(3,5-difluorobenzyl)-N-((ethoxycarbonyl)oxy)-2,2-dimethylbutanamide-3,4-d2

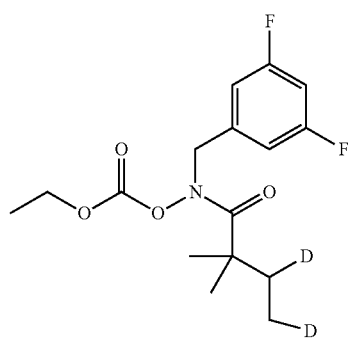 [SMILES: [2H]CC([2H])C(C)(C)C(=O)N(Cc1cc(F)cc(F)c1)OC(=O)OCC]

The titled compound 61 was prepared in 17% yield from N-(3,5-difluorobenzyl)-N-hydroxy-2,2-dimethylbutanamide-3,4-d2 (170 mg, 0.66 mmol), ethyl carbonochloridate (106 mg, 0.99 mmol), TEA (0.13 mL, 0.99 mmol) according to the procedure outlined for compound 50. $^1$H NMR (400 MHz, CDCl$_3$) δ 6.89-6.81 (m, 2H), 6.72 (tt, J=8.9, 2.3 Hz, 1H), 4.85 (s, 2H), 4.35 (q, J=7.1 Hz, 2H), 1.59-1.53 (m, 1H), 1.37 (t, J=7.1 Hz, 3H), 1.18 (s, 6H), 0.83-0.78 (m, 2H). LC-MS (m/z) 332.4 (M+H$^+$).

Compound 62: N-(3,5-difluorobenzyl)-2,2-dimethyl-N-(nicotinoyloxy)butanamide-3,4-d2

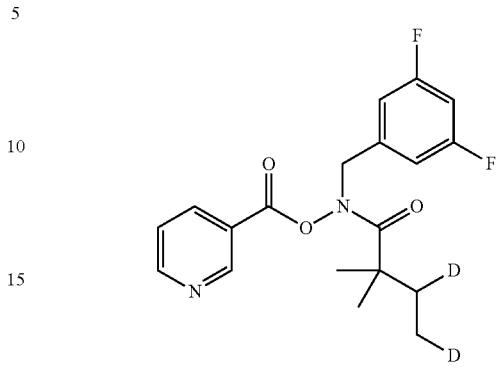

The titled compound 62 was prepared in 67% yield from N-(3,5-difluorobenzyl)-N-hydroxy-2,2-dimethylbutanamide-3,4-d2 (200 mg, 0.77 mmol), pyridine-3-carbonyl chloride hydrochloride (150 mg, 0.84 mmol) and TEA (0.22 ml, 1.54 mmol) according to the procedure outlined for compound 50. $^1$H NMR (400 MHz, CDCl$_3$) δ (ppm): 9.20 (s, 1H), 8.89 (d, J=4.0 Hz, 1H), 8.28 (dt, J=2.0, 8.0 Hz, 1H), 7.50 (dd, J=4.8, 8.0 Hz, 1H), 6.83-6.89 (m, 2H), 6.71-6.77 (m, 1H), 4.97 (s, 2H), 1.53-1.59 (m, 1H), 1.20 (s, 6H), 0.82-0.86 (m, 2H). LC-MS (m/z) 365.4 (M+H$^+$).

Compound 63: ((N-benzyl-2,2-dimethylbutanamido)oxy)methyl pivalate

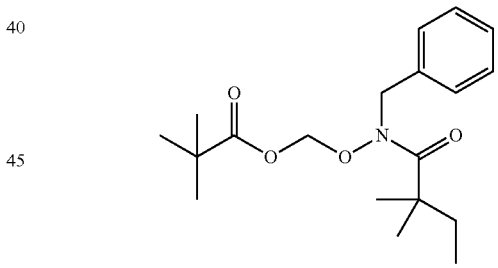

Into a 50 ml 3-necked round bottom flask, purged and maintained with an inert atmosphere of nitrogen, was placed with N-benzyl-N-hydroxy-2,2-dimethylbutanamide (880 mg, 4 mmol), K$_2$CO$_3$ (1.1 g, 8 mmol) and DMF (10 mL). The resulting solution was stirred for 10 min at room temperature. This was followed by the addition of chloromethyl pivalate (1.8 g, 12 mmol) in DMF (5 ml) with dropwise at room temperature. The mixture was stirred for another 4 h. The mixture were extracted with EtOAc and the combined organic layer washed with brine, dried (Na$_2$SO4) and concentrated in vacuo. Purification by silica gel chromatography (EA/PE=1/20) to give compound 63 (100 mg, 7.4%). $^1$H NMR (400 MHz, CDCl$_3$) δ (ppm): 7.27-7.33 (m, 4H), 7.22-7.25 (m, 1H), 5.63 (s, 2H), 4.92 (s, 2H), 1.61 (q, J=7.6 Hz, 2H), 1.20 (s, 9H), 1.19 (s, 6H), 0.75 (t, J=7.6 Hz, 3H). LC-MS (m/z) 336.4 (M+H$^+$).

Compound 64: ((N-(3,5-difluorobenzyl)-2,2-dimethylbutanamido-3,4-d2)oxy)methyl pivalate

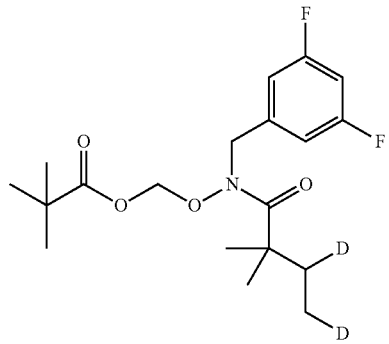 [SMILES: [2H]CC([2H])C(C)(C)C(=O)N(Cc1cc(F)cc(F)c1)OCOC(=O)C(C)(C)C]

The titled compound 64 was prepared in 12.5% yield from N-(3,5-difluorobenzyl)-N-hydroxy-2,2-dimethylbutanamide-3,4-d2 (150 mg, 0.58 mmol), chloromethyl pivalate (173 mg, 1.16 mmol), Cs$_2$CO$_3$ (282 mg, 0.87 mmol) and pyridine (22.8 mg, 0.5 mmol) according to the procedure outlined for compound 63. $^1$H NMR (400 MHz, CDCl$_3$) δ (ppm): 6.82-6.87 (m, 2H), 6.67-6.73 (m, 1H), 5.64 (s, 2H), 4.87 (s, 2H), 1.58-1.62 (m, 1H), 1.20 (s, 6H), 1.19 (s, 9H), 0.75-0.79 (m, 2H). LC-MS (m/z) 374.4 (M+H$^+$).

Compound 65: N-(3,5-difluorobenzyl)-N-(((2-methoxyethoxy)carbonyl)oxy)-2,2-dimethylbutanamide-3,4-d2

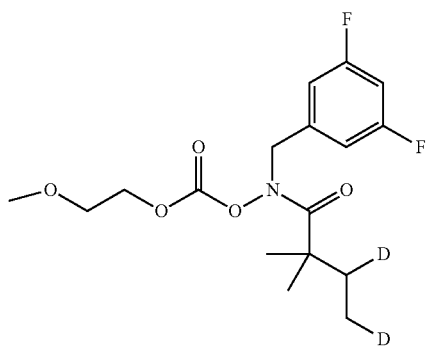 [SMILES: [2H]CC([2H])C(C)(C)C(=O)N(Cc1cc(F)cc(F)c1)OC(=O)OCCOC]

The titled compound 65 was prepared in yield from N-(3,5-difluorobenzyl)-N-hydroxy-2,2-dimethylbutanamide-3,4-d2 (150 mg, 0.58 mmol), 2-methoxyethyl carbonochloridate (173 mg, 1.16 mmol) according to the procedure outlined for compound 50. 1H NMR (400 MHz, CDCl$_3$) δ 6.86-6.79 (m, 2H), 6.70 (tt, J=8.9, 2.3 Hz, 1H), 4.83 (s, 2H), 4.45-4.40 (m, 2H), 3.64-3.59 (m, 2H), 3.37 (s, 3H), 1.57-1.51 (m, 1H), 1.16 (s, 6H), 0.81-0.73 (m, 2H). LC-MS (m/z) 362.4 (M+H$^+$).

Compound 66: N-(3,5-difluorobenzyl)-N-(((2-(2-methoxyethoxy)ethoxy)carbonyl)oxy)-2,2-dimethylbutanamide-3,4-d2

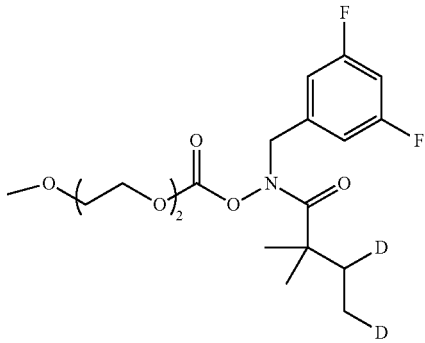

Into a 50 ml 3-necked round bottom flask, purged and maintained with an inert atmosphere of nitrogen, was placed with 2-(2-methoxyethoxy)ethan-1-ol (360 mg, 3 mmol), pyridine (284 mg, 3.6 mmol) and DCM (10 mL), and followed by the addition of triphosgene (311 mg, 1.05 mmol) at 0° C. The mixture was stirred at room temperature for 1 h. To this solution was added N-(3,5-difluorobenzyl)-N-hydroxy-2,2-dimethylbutanamide-3,4-d2 (520 mg, 2 mmol) and TEA (455 mg, 4.5 mmol) in DCM (2 mL). The mixture was stirred at room temperature for 3 h, was extracted with DCM and the combined organic layer washed with brine, dried (Na$_2$SO4) and concentrated in vacuo. Purification by silica gel chromatography (EA/PE=1/3) to give compound 66 (700 mg, 86%) as a light red oil. 1H NMR (400 MHz, CDCl$_3$) δ 6.88-6.82 (m, 2H), 6.76-6.68 (m, 1H), 4.85 (s, 2H), 4.48-4.43 (m, 2H), 3.80-3.72 (m, 2H), 3.66-3.63 (m, 2H), 3.57-3.52 (m, 2H), 3.37 (s, 3H), 1.59-1.52 (m, 1H), 1.18 (s, 6H), 0.80 (q, J=7.0 Hz, 2H). LC-MS (m/z) 406.4 (M+H$^+$).

Compound 67: N-((2,5,8,11-tetraoxadodecanoyl)oxy)-N-(3,5-difluorobenzyl)-2,2-dimethylbutanamide-3,4-d2

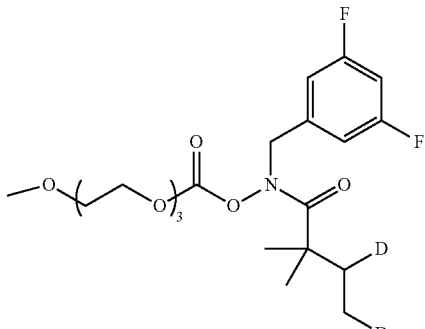

The titled compound 67 was prepared in 8% yield from N-(3,5-difluorobenzyl)-N-hydroxy-2,2-dimethylbutanamide-3,4-d2 (520 mg, 2 mmol), pyridine (758 mg), triphosgene (758 mg) and 2-(2-(2-methoxyethoxy)ethoxy)ethan-1-ol (1.3 g, 8 mmol) according to the procedure outlined for compound 66. 1H NMR (400 MHz, CDCl$_3$) δ 6.87-6.80 (m, 2H), 6.70 (tt, J=8.9, 2.3 Hz, 1H), 4.83 (s, 2H), 4.44-4.40 (m, 2H), 3.76-3.72 (m, 2H), 3.68-3.59 (m, 6H), 3.53-3.50 (m, 2H), 3.35 (s, 3H), 1.57-1.51 (m, 1H), 1.16 (s, 6H), 0.80-0.75 (m, 2H). LC-MS (m/z) 405.5 (M+H⁺).

Compound 68: N-benzyl-N-((bis(dimethylamino)phosphoryl)oxy)-2,2-dimethylbutanamide

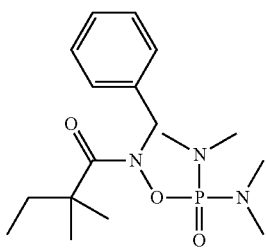 [SMILES: CCC(C)(C)C(=O)N(Cc1ccccc1)OP(=O)(N(C)C)N(C)C]

N-benzyl-N-hydroxy-2,2-dimethylbutanamide (221 mg) was dissolved in 4 ml of dry DMF, 60 mg of NaH (60% in oil) was added at 0° C. under N₂ and stirred for 30 min. N,N,N',N'-Tetramethylphosphorodiamidic chloride (116 mg) was added and the mixture was allowed to warm to room temperature and stirred for 11 h. The mixture was quenched with cold water and extracted with EA, the combined organic layers was washed with water, brine, dried over Na₂SO₄, concentrated and the residue was purified by silica gel column chromatography to give the product 68 (106.5 mg, 30%). ¹H NMR (400 MHz, CDCl₃) δ (ppm): 7.27-7.35 (m, 5H), 5.19 (s, 2H), 2.76 (s, 3H), 2.72 (s, 3H), 2.57 (s, 3H), 2.54 (s, 3H), 1.66 (q, J=7.6 Hz, 2H), 1.26 (s, 6H), 0.93 (t, J=7.6 Hz, 3H). LC-MS (m/z) 356.4 (M+H⁺).

Compound 69: dibenzyl (((N-benzyl-2,2-dimethylbutanamido)oxy)methyl)phosphate

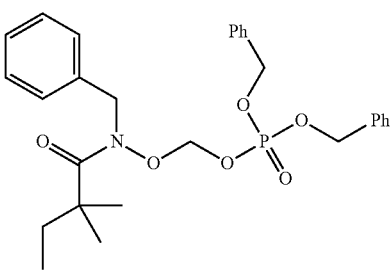 [SMILES: CCC(C)(C)C(=O)N(Cc1ccccc1)OCOP(=O)(OCc1ccccc1)OCc1ccccc1]

The titled compound 69 was prepared in 28% yield from N-benzyl-N-hydroxy-2,2-dimethylbutanamide (221 mg, 1 mmol), pyridine (758 mg), NaH (60 mg) and dibenzyl (chloromethyl) phosphate (424.7 mg, 1.3 mmol) according to the procedure outlined for compound 68. ¹H NMR (400 MHz, CDCl₃) δ (ppm): 7.33-7.37 (m, 10H), 7.27-7.30 (m, 5H), 5.64 (s, 1H), 5.60 (s, 1H), 5.40 (s, 1H), 5.37 (s, 1H), 5.11 (s, 1H), 5.09 (s, 1H), 4.90 (s, 2H), 1.55 (q, J=7.6 Hz, 2H), 1.14 (s, 6H), 0.75 (t, J=7.6 Hz, 3H). LC-MS (m/z) 512.6 (M+H⁺).

Compound 70: dimethyl ((N-benzyl-2,2-dimethylbutanamido)oxy)phosphonate

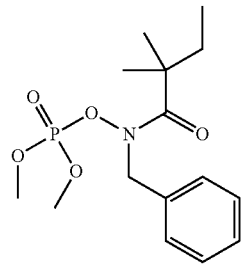 [SMILES: CCC(C)(C)C(=O)N(Cc1ccccc1)OP(=O)(OC)OC]

The titled compound 70 was prepared in 56% yield from N-benzyl-N-hydroxy-2,2-dimethylbutanamide (221 mg, 1 mmol), dimethyl phosphorochloridate (173.38 mg, 1.2 mmol) and pyridine (0.12 ml, 1.5 mmol) according to the procedure outlined for compound 50. ¹H NMR (400 MHz, CDCl₃) δ (ppm): 7.28-7.37 (m, 5H), 5.07 (s, 2H), 3.79 (s, 3H), 3.76 (s, 3H), 1.64 (q, J=7.6 Hz, 2H), 1.21 (s, 6H), 0.81 (t, J=7.6 Hz, 3H). LC-MS (m/z) 333.3 (M+H⁺).

Compound 71: ((N-benzyl-2,2-dimethylbutanamido)oxy)phosphonic acid

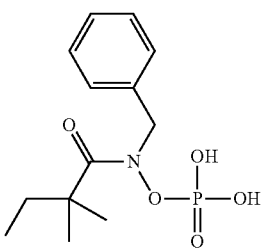 [SMILES: CCC(C)(C)C(=O)N(Cc1ccccc1)OP(=O)(O)O]

To a cooled solution of N-benzyl-N-hydroxy-2,2-dimethylbutanamide (318 mg, 1.44 mmol) and TEA (0.2 mL, 1.44 mmol) in 5 ml of dry DCM was added phosphoryl trichloride (0.13 mL, 1.44 mmol). The mixture was stirred at room temperature for 2 h, and 0.5 mL of water was added and keep stirring for 2 h. The mixture were extracted with DCM and the combined organic layer washed with brine, dried (Na₂SO4) and concentrated in vacuo. Purification by Pre-HPLC to give compound (30 mg, 7%). ¹H NMR (400 MHz, CDCl₃) δ 7.34 (d, J=6.5 Hz, 2H), 7.22-7.17 (m 3H), 5.04 (s, 2H), 1.65-1.54 (m, 2H), 1.14 (s, 6H), 0.66 (t, J=7.4 Hz, 3H). LC-MS (m/z) 300.1 (M+H⁻).

Compound 72: N-benzyl-2,2-dimethyl-N-((5-((3aS,4S,6aR)-2-oxohexahydro-1H-thieno[3,4-d]imidazol-4-yl)pentanoyl)oxy)butanamide

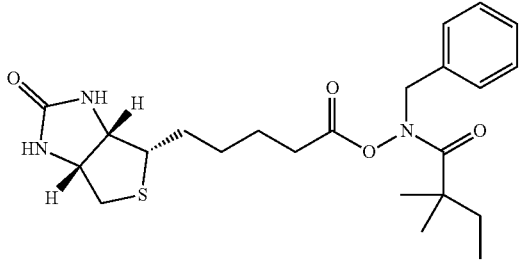 [SMILES: CCC(C)(C)C(=O)N(Cc1ccccc1)OC(=O)CCCC[C@@H]1SC[C@@H]2NC(=O)N[C@@H]21]

A mixture of N-benzyl-N-hydroxy-2,2-dimethylbutanamide (110.5 mg), biotin-COOH (183 mg) and N-(3-Dimethylaminopropyl)-N'-ethylcarbodiimide hydrochloride (191.7 mg) were dissolved in dry DMF (10 mL), and 0.45 mL of DIEA was added. The reaction mixtures were stirred at 50° C. for 24 h. The mixture was extracted with EtOAc, washed with water and brine, dried (Na$_2$SO4), and concentrated in vacuo. Purification by pre-HPLC to give compound 72 (72 mg, 32%). 1H NMR (400 MHz, CDCl$_3$) δ 7.42-7.22 (m, 6H), 5.56 (bs, 1H), 4.94 (s, 2H), 4.42 (d, J=87.7 Hz, 2H), 3.13 (bs, 1H), 2.93 (d, J=12.1 Hz, 1H), 2.75 (d, J=11.9 Hz, 1H), 2.36 (t, J=7.0 Hz, 2H), 1.67 (bs, 4H), 1.60-1.55 (m, 2H), 1.44 (bs, 2H), 1.20 (s, 6H), 0.85 (t, J=7.4 Hz, 3H). LC-MS (m/z) 448.6 (M+H$^+$).

Compound 73: N-benzyl-N-((4-hydroxybenzyl)oxy)-2,2-dimethylbutanamide

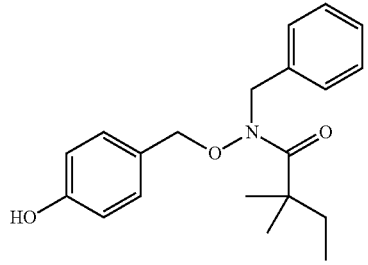 [SMILES: CCC(C)(C)C(=O)N(Cc1ccccc1)OCc1ccc(O)cc1]

Into a 50 ml 3-necked round bottom flask, purged and maintained with an inert atmosphere of nitrogen, was placed with N-benzyl-N-hydroxy-2,2-dimethylbutanamide (330 mg) and dry DMF (10 mL). To this mixture was added NaH (120 mg, 60% in oil). The reaction mixtures were stirred at room temperature for 30 min, and followed by addition of 4-(bromomethyl)phenyl acetate (510 mg). The mixture was stirred at room temperature for 3 h and 40° C. for 30 min, then added 1 ml of water and stirred for 2 h. The mixture was extracted with EtOAc, washed with water and brine, dried (Na$_2$SO4), and concentrated in vacuo. Purification by silica gel column (EA/PE=1/6) to give compound 73 (300 mg, 61.4%) as a colorless oil. $^1$H NMR (400 MHz, CDCl$_3$) δ 7.34-7.25 (m, 4H), 7.12 (d, J=8.5 Hz, 2H), 6.78 (d, J=8.6 Hz, 1H), 4.87 (s, 2H), 4.75 (s, 2H), 1.64 (q, J=7.5 Hz, 2H), 1.21 (s, 5H), 0.79 (t, J=7.5 Hz, 3H). LC-MS (m/z) 328.4 (M+H$^+$).

Compound 74: N-benzyl-3,3-difluoro-N-hydroxy-2,2-dimethylpropanamide

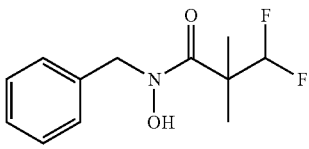 [SMILES: CC(C)(C(=O)N(O)Cc1ccccc1)C(F)F]

The titled compound 74 was prepared in 53% yield from n-benzylhydroxylamine hydrochloride (127 mg), 3,3-difluoro-2,2-dimethylpropanoic acid (110 mg), and oxalyl chloride (152 mg) according to the procedure outlined for compound 32. $^1$H NMR (400 MHz, CDCl$_3$) δ (ppm): 7.34-7.41 (m, 3H), 7.29-7.32 (m, 2H), 6.27 (t, J=56.8 Hz, 1H), 4.87 (s, 2H), 1.38 (t, J=1.2 Hz, 6H). LC-MS (m/z) 244.3 (M+H$^+$).

Compound 75: N-(3,5-difluorobenzyl)-3,3-difluoro-N-hydroxy-2,2-dimethylpropanamide

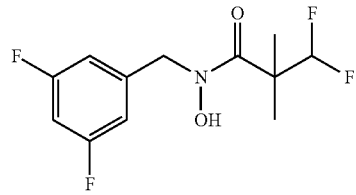

The titled compound 75 was prepared in 50% yield from N-(3,5-difluorobenzyl)hydroxylamine (127 mg), 3,3-difluoro-2,2-dimethylpropanoic acid (110 mg), and oxalyl chloride (152 mg) according to the procedure outlined for compound 32. $^1$H NMR (400 MHz, CDCl$_3$) δ (ppm): 6.82-6.86 (m, 2H), 6.74-6.81 (m, 1H), 6.25 (t, J=56.8 Hz, 1H), 4.83 (s, 2H), 1.39 (t, J=1.2 Hz, 6H). LC-MS (m/z) 280.2 (M+H$^+$).

Compound 76: N-(3,5-difluorobenzyl)-4-fluoro-N-hydroxy-2,2-dimethylbutanamide

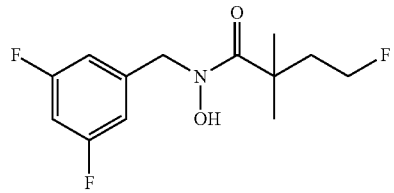 [SMILES: CC(C)(CCF)C(=O)N(O)Cc1cc(F)cc(F)c1]

The titled compound 76 was prepared in 50% yield from N-(3,5-difluorobenzyl)hydroxylamine (361 mg), 3,3-difluoro-2,2-dimethylpropanoic acid (330 mg), and oxalyl chloride (343 mg) according to the procedure outlined for compound 32. $^1$H NMR (400 MHz, CDCl$_3$) δ 6.85-6.79 (m, 2H), 6.72 (tt, J=8.9, 2.3 Hz, 1H), 4.78 (s, 2H), 4.62 (t, J=5.6 Hz, 1H), 4.50 (t, J=5.6 Hz, 1H), 2.15 (t, J=5.6 Hz, 11H), 2.08 (t, J=5.6 Hz, 1H), 1.33 (s, 6H). LC-MS (m/z) 276.3 (M+H$^+$).

Compound 77:
N-benzyl-2,2-dimethyl-N-(pivaloyloxy)butanamide

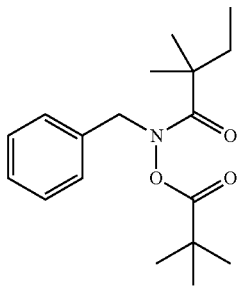

The titled compound 77 was prepared in 66% yield from N-benzyl-N-hydroxy-2,2-dimethylbutanamide (221 mg, 1 mmol), pivaloyl chloride (144 mg, 1.2 mmol) and pyridine (0.12 ml, 1.5 mmol) according to the procedure outlined for compound 50. $^1$H NMR (400 MHz, CDCl$_3$) δ 7.32-7.25 (m, 2H), 7.25 (t, J=1.5 Hz, 1H), 7.24-7.22 (m, 1H), 5.70 (s, 1H), 4.89 (s, 2H), 1.55 (q, J=7.5 Hz, 2H), 1.17 (s, 5H), 1.14 (s, 8H), 0.84 (t, J=7.5 Hz, 3H). LC-MS (m/z) 306.4 (M+H$^+$).

Compound 79: tert-butyl (S)-(1-((N-benzyl-2,2-dimethylbutanamido)oxy)-3-methyl-1-oxobutan-2-yl)carbamate

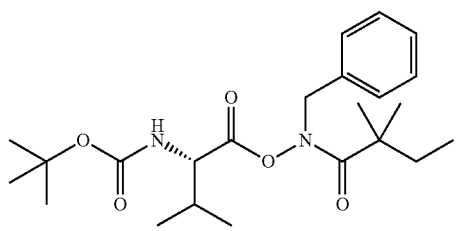 [SMILES: CCC(C)(C)C(=O)N(Cc1ccccc1)OC(=O)[C@@H](NC(=O)OC(C)(C)C)C(C)C]

A mixture of N-benzyl-N-hydroxy-2,2-dimethylbutanamide (221 mg, 1 mmol, 1 eq), N-Boc-L-valine (239.36 mg, 1.1 mmol, 1.1 eq), DCC (247.6 mg, 1.2 mmol) and DMAP (24.4 mg, 0.2 mmol, 0.2 eq) in dry DCM (10 mL) was stirred at room temperature for 16 h. The mixture were extracted with DCM and the combined organic layer washed with brine, dried (Na$_2$SO4) and concentrated in vacuo. Purification by silica gel chromatography (EA/PE=1/5) to give compound 79. $^1$H NMR (400 MHz, CDCl$_3$) δ 7.37-7.28 (m, 3H), 7.26 (dd, J=2.5, 0.9 Hz, 1H), 5.20 (d, J=15.7 Hz, 1H), 4.87 (d, J=9.6 Hz, 1H), 4.69 (d, J=15.6 Hz, 1H), 4.32 (dd, J=9.7, 4.8 Hz, 1H), 2.00 (dd, J=11.7, 6.8 Hz, 1H), 1.66-1.54 (m, 2H), 1.44 (s, 9H), 1.21 (d, J=8.1 Hz, 6H), 0.93 (d, J=6.8 Hz, 3H), 0.86-0.80 (m, 5H). LC-MS (m/z) 421.6 (M+H$^+$).

Compound 80:
N-((L-valyl)oxy)-N-benzyl-2,2-dimethylbutanamide

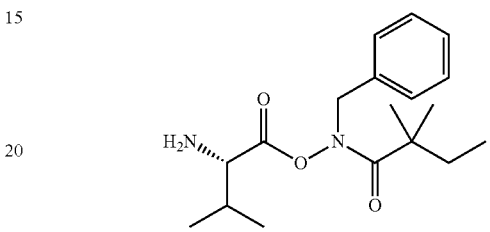

To a solution of compound (200 mg) was dissolved in DCM (4 mL) at 0° C. was added TFA (0.5 mL). the mixture was stirred at for 1 h and room temperature for 2 h. the mixture was neutralized with saturated aqueous NaHCO$_3$ and extracted with DCM and the combined organic layer washed with brine, dried (Na$_2$SO4) and concentrated in vacuo to give the product 80. $^1$H NMR (400 MHz, CDCl$_3$) δ 7.36-7.22 (m, 5H), 5.17 (d, J=15.7 Hz, 1H), 4.69 (d, J=15.7 Hz, 1H), 3.28 (d, J=4.7 Hz, 1H), 1.88 (ddd, J=13.7, 11.8, 6.8 Hz, 2H), 1.70-1.49 (m, 3H), 1.22-1.15 (m, 6H), 0.91 (d, J=6.8 Hz, 3H), 0.85 (t, J=7.5 Hz, 3H), 0.80 (d, J=6.8 Hz, 3H). LC-MS (m/z) 321.4 (M+H$^+$).

Compound 81: tert-butyl (S)-2-(((N-benzyl-2,2-dimethylbutanamido)oxy)carbonyl)pyrrolidine-1-carboxylate

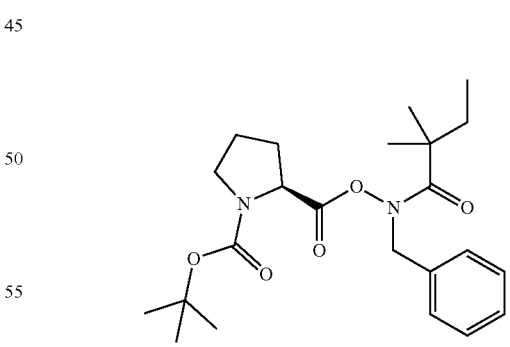

The titled compound 81 was prepared in 35% yield from N-benzyl-N-hydroxy-2,2-dimethylbutanamide (221 mg, 1 mmol), Boc-proline (236.7 mg, 1.1 mmol), DCC (247.6 mg, 1.2 mmol) and DMAP (24.4 mg, 0.2 mmol) according to the procedure outlined for compound 79. $^1$H NMR (400 MHz, CDCl$_3$) δ 7.36-7.29 (m, 5H), 4.94 (s, 2H), 4.41 (dd, J=8.6, 2.9 Hz, 1H), 3.48-3.41 (m, 2H), 2.14-2.04 (m, 2H), 1.86-1.76 (m, 2H), 1.65-1.56 (m, 2H), 1.45 (s, 9H), 1.21 (s, 6H), 0.83 (t, J=7.4 Hz, 3H). LC-MS (m/z) 419.5 (M+H$^+$).

Compound 82: N-benzyl-N-((dimethylglycyl)oxy)-2,2-dimethylbutanamide

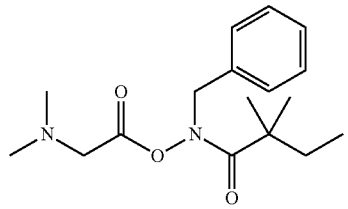 [SMILES: CCC(C)(C)C(=O)N(Cc1ccccc1)OC(=O)CN(C)C]

The titled compound 82 was prepared in 35% yield from N-benzyl-N-hydroxy-2,2-dimethylbutanamide (221 mg, 1 mmol), dimethylglycine (153.5 mg, 1.1 mmol), DCC (247.6 mg, 1.2 mmol) and DMAP (24.4 mg, 0.2 mmol) according to the procedure outlined for compound 79. $^1$H NMR (400 MHz, CDCl$_3$) δ 7.36-7.27 (m, 4H), 4.95 (s, 2H), 4.92 (s, 1H), 3.30 (s, 2H), 2.45 (s, 6H), 1.57 (q, J=7.5 Hz, 2H), 1.20 (s, 6H), 0.86 (t, J=7.5 Hz, 3H). LC-MS (m/z) 307.4 (M+H$^+$).

Compound 83: N-((L-seryl)oxy)-N-benzyl-2,2-dimethylbutanamide

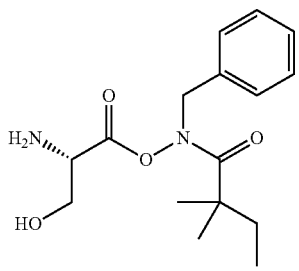 [SMILES: CCC(C)(C)C(=O)N(Cc1ccccc1)OC(=O)[C@@H](N)CO]

tert-butyl (S)-(1-((N-benzyl-2,2-dimethylbutanamido)oxy)-3-(tert-butoxy)-1-oxopropan-2-yl)carbamate was prepared in 35% yield from N-benzyl-N-hydroxy-2,2-dimethylbutanamide (221 mg, 1 mmol), Boc-L-Ser($^t$Bu)-OH (574.8 mg, 2.2 mmol), EDCI (460 mg, 2.4 mmol) according to the procedure outlined for compound 79.

The above N-Boc compound (200 mg) was dissolved in DCM (4 mL) at 0° C. was added TFA (0.5 mL). the mixture was stirred at for 1 h and room temperature for 2 h. the mixture was neutralized with saturated aqueous NaHCO$_3$ and extracted with DCM and the combined organic layer washed with brine, dried (Na$_2$SO4) and concentrated in vacuo to give the product 83. $^1$H NMR (400 MHz, CDCl$_3$) δ 7.33-7.25 (m, 5H), 5.04 (d, J=16.0 Hz, 1H), 4.85 (d, J=16.0 Hz, 1H), 4.23-4.13 (m, 1H), 4.03-3.88 (m, 2H), 1.64-1.54 (m, 2H), 1.19 (s, 6H), 0.84 (t, J=7.0 Hz, 3H). LC-MS (m/z) 309.4 (M+H$^+$).

Compound 84: N-benzyl-1-(5-fluoropyrimidin-2-yl)-N-hydroxypiperidine-4-carboxamide

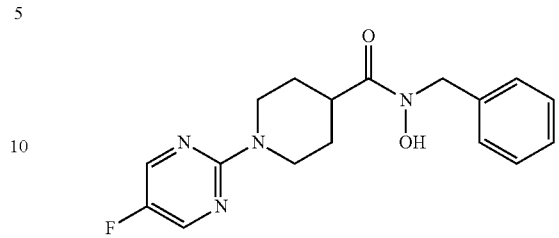

The titled compound 84 was prepared in 42% yield from n-benzylhydroxylamine hydrochloride (137 mg), 1-(5-fluoropyrimidin-2-yl)piperidine-4-carboxylic acid (195 mg), and oxalyl chloride (163 mg) according to the procedure outlined for compound 32. $^1$H NMR (400 MHz, CDCl$_3$) δ (ppm): 8.19 (s, 2H), 7.30-7.42 (m, 5H), 4.81-4.95 (m, 2H), 4.70 (d, J=12.8 Hz, 2H), 2.85-3.02 (m, 2H), 2.61-2.82 (m, 1H), 1.75-1.92 (m, 4H). LC-MS (m/z) 331.4 (M+H$^+$).

Compound 85: N-(4-fluorobenzyl)-1-(5-fluoropyrimidin-2-yl)-N-hydroxypiperidine-4-carboxamide

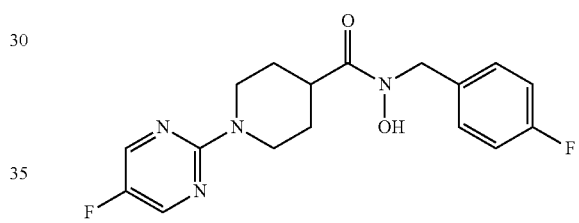

The titled compound 85 was prepared in 40% yield from N-(4-fluorobenzyl)hydroxylamine (106 mg), 1-(5-fluoropyrimidin-2-yl)piperidine-4-carboxylic acid (200 mg), and oxalyl chloride (169 mg) according to the procedure outlined for compound 32. $^1$H NMR (400 MHz, CDCl$_3$) δ 8.21 (s, 2H), 7.32-7.25 (m, 2H), 7.06-7.02 (m, 2H), 4.83 (s, 2H), 4.70 (d, J=13.6 Hz, 2H), 3.09-2.88 (m, 3H), 1.96-1.69 (m, 4H). LC-MS (m/z) 349.4 (M+H$^+$).

Compound 86: N-(3,5-difluorobenzyl)-1-(5-fluoropyrimidin-2-yl)-N-hydroxypiperidine-4-carboxamide

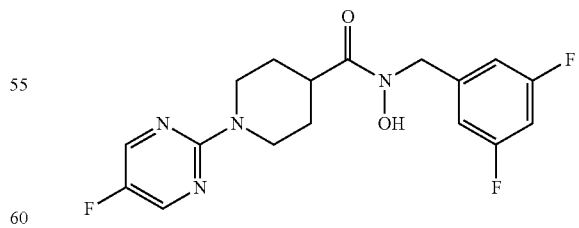

The titled compound 86 was prepared in 38% yield from N-(3,5-difluorobenzyl)hydroxylamine (119 mg), 1-(5-fluoropyrimidin-2-yl)piperidine-4-carboxylic acid (200 mg), and oxalyl chloride (169 mg) according to the procedure outlined for compound 32. 1H NMR (400 MHz, CDCl$_3$) δ 8.18 (s, 2H), 6.78-6.72 (dd, J=7.5, 1.7 Hz, 1H), 6.78-6.72

(m, 1H), 4.83 (s, 2H), 4.70 (d, J=13.6 Hz, 2H), 3.04-2.86 (m, 3H), 1.90-1.70 (m, 4H). LC-MS (m/z) 367.4 (M+H$^+$).

Compound 87: N-(3,5-difluorobenzyl)-N-((ethoxycarbonyl)oxy)-2,2-dimethylbutanamide

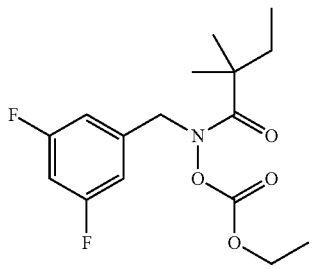 [SMILES: CCOC(=O)ON(Cc1cc(F)cc(F)c1)C(=O)C(C)(C)CC]

The titled compound 87 was prepared in 87% yield from N-(3,5-difluorobenzyl)-N-hydroxy-2,2-dimethylbutanamide (500 mg), ethyl carbonochloridate (232.24 mg), TEA (0.5 mL) according to the procedure outlined for compound 50. 1H NMR (400 MHz, CDCl3) δ 6.87-6.77 (m, 2H), 6.70 (ddd, J=8.9, 5.6, 2.3 Hz, 1H), 4.83 (s, 2H), 4.33 (q, J=7.1 Hz, 2H), 1.56 (q, J=7.5 Hz, 2H), 1.35 (t, J=7.1 Hz, 3H), 1.17 (s, 6H), 0.79 (t, J=7.5 Hz, 3H). LC-MS (m/z) 330.4 (M+H$^+$).

In Vivo Pharmacology

Effect on Mouse EAE Model

A mouse EAE model of multiple sclerosis was established by immunizing C57/BL6 mice with MOG35-55 (amino acids 35-55 of myelin oligodendrocyte glycoprotein) to induce autoimmune reaction to the myelin of the CNS. Immune reaction causes damage to the myelin, and subsequently the neurons, resulting in animal paralysis.

SIR1-365 was delivered by food at 10 g/kg and FTY-720 was used as a positive control. Mice were feed with FTY-720 containing drinking water or with SIR1-365 containing chow 2 days before 1st immunization for 28 consecutive days. Scoring started at Day 8 post-1st immunization. The results indicated that SIR1-365 significantly reduced the disease score in EAE mice.

The results of pathological studies indicated myelin destruction of the spinal cord was protected by SIR1-365. Three different spinal cord regions were sectioned and stained with hematoxylin and eosin (H&E), spinal cord damages were scored and quantified. Feeding with SIR1-365 containing food protected spinal cord damage induced by auto-immune reaction in EAE model. SIR1-365 feeding with 10 g/kg in food (10 g of compound per kilogram food) significantly reduced EAE-induced myelin damage and animal paralysis.

Conclusion: In a mouse multiple sclerosis model, SIR1-365 demonstrated substantial reduction of myelin damage induced by autoimmunity.

Effect on Mouse SIRS Model Sepsis preceded by systemic inflammatory response syndrome (SIRS), is a major cause of death in critically ill patients. TNF-α functions as a key mediator in SIRS pathogenesis by the induction of RIP1-RIP3 mediated necroptosis of the liver. Blockage of RIP1's kinase activity either genetically or by selective inhibitor prevented TNF-α-induced SIRS in mice.

SIR1-365 was administrated as a single dose by oral gavage at 3 different doses: 1, 3, and 10 mg/kg to C57Bl/6J mice. TNF-α was delivered intravenously 2 minutes after SIR1-365 administration. 87.5% (7 of 8) mice in the control group (given vehicle) died within 36 hours, whereas 50% (4 of 8) mice given SIR1-365 at 1 mg/kg and 25% (2 of 8) mice given SIR1-365 at 3 mg/kg died in the same period. However, 10 mg/kg of SIR1-365 completely prevented mortality caused by SIRS.

Conclusion: In C57Bl/6J mice, oral administration of SIR1-365 prevented TNFα-induced mortality in a dose-dependent manner, with complete prevention at dose of 10 mg/kg.

| Cmpd ID | Cmpd No WO2016/ 101885 | Structure | EC50/ nM (HT-29) | Human Liver Microsome T$_{1/2}$ (min) | Rat Liver Microsome T$_{1/2}$ (min) | Mouse Liver Microsome T$_{1/2}$ (min) | Dog Liver Microsome T$_{1/2}$ (min) | Monkey Liver Microsome T$_{1/2}$ (min) |
|---|---|---|---|---|---|---|---|---|
| SIR1-365 | 13 PCT/CN2018/116555 | 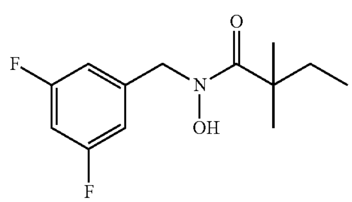 [SMILES: CCC(C)(C)C(=O)N(O)Cc1cc(F)cc(F)c1] | 28 | 228 | 20 | 17 | 2 | 5 |
| SIR1-165 | 92 | 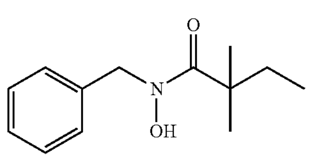 [SMILES: CCC(C)(C)C(=O)N(O)Cc1ccccc1] | 25 | 204 | 25 | 32 | 7 | 3 |
| SIR1-181 | 94 | 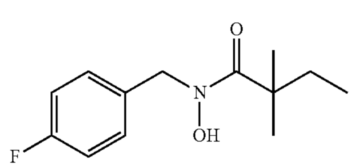 [SMILES: CCC(C)(C)C(=O)N(O)Cc1ccc(F)cc1] | 64 | 178 | 37 | 24 | NA | NA |

| Cmpd ID | Cmpd No WO2016/ 101885 | Structure | EC50/ nM (HT-29) | Human T₁/₂ (min) | Rat T₁/₂ (min) | Mouse T₁/₂ (min) | Dog T₁/₂ (min) | Monkey T₁/₂ (min) |
|---|---|---|---|---|---|---|---|---|
| SIR1-186 | 99 | (3,4,5-trifluorobenzyl N-hydroxy 2,2-dimethylbutanamide) | 46 | 64 | 21 | 6 | NA | NA |
| SIR1-179 | 96 | (2,4-difluorobenzyl N-hydroxy 2,2-dimethylbutanamide) | 197 | 198 | 28 | 23 | NA | NA |
| SIR1-180 | 95 | (3,4-difluorobenzyl N-hydroxy 2,2-dimethylbutanamide) | 55 | 107 | 29 | 11 | NA | NA |
| SIR1-184 | 97 | (2,3,4-trifluorobenzyl N-hydroxy 2,2-dimethylbutanamide) | 272 | 36 | 19 | 12 | NA | NA |
| SIR1-176 | 93 | (2,3,5-trifluorobenzyl N-hydroxy 2,2-dimethylbutanamide) | 65 | 67 | 22 | 9 | NA | NA |

| Cmpd ID | Cmpd No WO2016/ 101885 | Structure | EC50/ nM (HT-29) | Hepatocyte Stability | | | | |
|---|---|---|---|---|---|---|---|---|
| | | | | Human T₁/₂ (min) | Rat T₁/₂ (min) | Mouse T₁/₂ (min) | Dog T₁/₂ (min) | Monkey T₁/₂ (min) |
| SIR1-365 | 13 PCT/CN2 018/ 116555 | (3,5-difluorobenzyl N-hydroxy 2,2-dimethylbutanamide) | 28 | 152 | 28 | 20 | 13 | 25 |
| SIR1-165 | 92 | (benzyl N-hydroxy 2,2-dimethylbutanamide) | 25 | 73 | 14 | 24 | 14 | 19 |

| Cmpd No | SIR1-165 | | | | SIR1-365 | | | |
|---|---|---|---|---|---|---|---|---|
| Species | Mouse | Rat | Dog | Monkey | Mouse | | Rat | |
| Dose (IV) (mg/kg) | 2 | 2 | 3 | 2 | 2 | | 2 | |
| $T_{1/2}$ (h) | 3.1 | 0.3 | 1.2 | 0.77 | 0.29 | | 0.59 | |
| $AUC_{0\text{-}inf}$ (ng · h/ml) | 323 | 520 | 1963 | 1940 | 489 | | 540 | |
| $Vd_{ss}$ (L/kg) | 3.08 | 1.2 | 1.24 | 0.86 | 1.7 | | 1.9 | |
| CL (mL · $kg^{-1}$ · $min^{-1}$) | 103 | 64 | 25.6 | 17.6 | 68.2 | | 61.7 | |
| Dose (PO) (mg/kg) | 10 | 10 | 10 | 10 | 10 | 40 | 20 | 60 |
| $T_{1/2}$ (h) | 1.6 | 0.8 | 1.35 | 0.73 | 0.48 | 0.83 | 1.4 | 1.2 |
| $C_{max}$ (ng/ml) | 249 | 148 | 171 | 185 | 1004 | 5423 | 1571 | 4906 |
| $AUC_{0\text{-}inf}$ (ng · h/ml) | 349 | 214 | 136 | 374 | 823 | 5409 | 1576 | 7525 |
| F (%) | 21.6 | 1.2 | 1.95 | 2.6 | 33.7 | 55.4 | 39.4 | 62.8 |

| Cmpd No | SIR1-365 | | | | SIRI-181 | | |
|---|---|---|---|---|---|---|---|
| Species | Dog | | Monkey | | Mouse | Rat | Dog |
| Dose (IV) (mg/kg) | 2 | | 2 | | 2 | | 5 |
| $T_{1/2}$ (h) | 1.02 | | 11.2 | | 0.595 | | 2 |
| $AUC_{0\text{-}inf}$ (ng · h/ml) | 1840 | | 1760 | | 522 | | 3210 |
| $Vd_{ss}$ (L/kg) | 0.73 | | 0.93 | | 3.28 | | 1.8 |
| CL (mL · $kg^{-1}$ · $min^{-1}$) | 18.5 | | 19.3 | | 63.71 | | 25.9 |
| Dose (PO) (mg/kg) | 10 | 60 | 150 | 30 | 100 | 200 | 10 | 10 | 10 |
| $T_{1/2}$ (h) | 7.15 | 5.65 | 11.9 | 1.50 | 1.77 | 2.16 | 0.513 | 0.541 | 4.6 |
| $C_{max}$ (ng/ml) | 981 | 938 | 2443 | 3730 | 10700 | 20600 | 2850 | 32.3 | 195 |
| $AUC_{0\text{-}inf}$ (ng · h/ml) | 1320 | 2050 | 7232 | 6930 | 41600 | 87200 | 1737 | 24.3 | 147.9 |
| F (%) | 14.9 | 4.06 | 5.33 | 26.3 | 47.5 | 49.5 | 66.6 | NA | 2.5 |

What is claimed is:

1. An amide compound of structure:

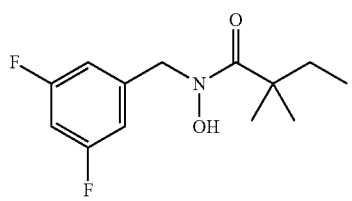 [SMILES: CCC(C)(C)C(=O)N(O)Cc1cc(F)cc(F)c1]

or a pharmaceutically acceptable salt, hydrate, or stereoisomer thereof.

2. A pharmaceutical composition comprising a compound of claim 1, and one or more pharmaceutically acceptable excipients.

3. A pharmaceutical composition comprising a therapeutically effective amount of a compound of claim 1, in unit dosage form and one or more pharmaceutically acceptable excipients.

4. A method of inhibiting necrosis, ferroptosis or human receptor interacting protein 1 kinase (RIP1), comprising administering to a person in need thereof a compound of claim 1.

* * * * *